United States Patent
Zhang et al.

(10) Patent No.: US 10,463,641 B2
(45) Date of Patent: *Nov. 5, 2019

(54) METHOD FOR USING SMALL MOLECULE COMPOUNDS TO INDUCE HUMAN TUMOR CELLS TO BE DIRECTLY REPROGRAMMED INTO NON-ONCOGENIC CELLS

(71) Applicant: Transcend Cytotherapy Co., Ltd, Jiangsu (CN)

(72) Inventors: Pei-Lin Zhang, Jiangsu (CN); Hong-Yang Wang, Shanghai (CN)

(73) Assignee: Transcend Cytotherapy Co., Ltd, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/780,398

(22) PCT Filed: Nov. 30, 2016

(86) PCT No.: PCT/CN2016/107910
§ 371 (c)(1),
(2) Date: May 31, 2018

(87) PCT Pub. No.: WO2017/092663
PCT Pub. Date: Jun. 8, 2017

(65) Prior Publication Data
US 2018/0353454 A1    Dec. 13, 2018

(30) Foreign Application Priority Data

Dec. 1, 2015 (CN) .......................... 2015 1 0869117

(51) Int. Cl.
| | | |
|---|---|---|
| *A61K 31/203* | (2006.01) |
| *A61K 45/06* | (2006.01) |
| *A61K 31/443* | (2006.01) |
| *A61K 31/4725* | (2006.01) |
| *A61K 31/506* | (2006.01) |
| *A61K 31/519* | (2006.01) |
| *A61P 35/00* | (2006.01) |
| *C12N 5/09* | (2010.01) |

(52) U.S. Cl.
CPC .......... *A61K 31/203* (2013.01); *A61K 31/443* (2013.01); *A61K 31/4725* (2013.01); *A61K 31/506* (2013.01); *A61K 31/519* (2013.01); *A61K 45/06* (2013.01); *A61P 35/00* (2018.01); *C12N 5/0693* (2013.01)

(58) Field of Classification Search
CPC .................................................... A61K 31/203
USPC ........................................................ 514/275
See application file for complete search history.

(56) References Cited

FOREIGN PATENT DOCUMENTS

| | | | | |
|---|---|---|---|---|
| CN | 102260646 A | * | 11/2011 | |
| CN | 102260646 A | | 11/2011 | |
| CN | 102604894 A | | 7/2012 | |
| CN | 103333920 A | | 10/2013 | |
| CN | 103627671 A | | 3/2014 | |
| CN | 103720689 A | | 4/2014 | |
| CN | 104278008 A | | 1/2015 | |
| WO | 2012014207 A2 | | 2/2012 | |
| WO | WO-2015061568 A1 | * | 4/2015 | ........... C12N 5/0657 |
| WO | 2015180636 A1 | | 12/2015 | |

OTHER PUBLICATIONS

English Translation of CN 102260646 A (2011).*
Rohwedel et al. "Induction of Cellular Differentiation by Retinoic Acid in Vitro". Cells Tissues Organs 1999;165: 190-202.

* cited by examiner

*Primary Examiner* — Kevin E Weddington
(74) *Attorney, Agent, or Firm* — Banner & Witcoff, Ltd.

(57) ABSTRACT

The disclosure includes a method of inducing direct reprogramming (transdifferentiation) into non-oncogenic cells accompanied by tumor cell apoptosis in human tumor cells using a small molecule composition, based on the mechanism of chemical-induction of direct cellular reprogramming. The disclosure also includes a small molecule composition used for the method, and culture media and agents prepared from the composition.

13 Claims, 9 Drawing Sheets

METHOD FOR USING SMALL MOLECULE COMPOUNDS TO INDUCE HUMAN TUMOR CELLS TO BE DIRECTLY REPROGRAMMED INTO NON-ONCOGENIC CELLS

RELATED APPLICATION DATA

This application is a National Stage Application under 35 U.S.C. 371 of co-pending PCT application number PCT/CN2016/107910 designating the United States and filed Nov. 30, 2016; which claims the benefit of CN Application number 201510869117.8 and filed Dec. 1, 2015 each of which are hereby incorporated by reference in their entireties.

TECHNICAL FIELD

This disclosure relates generally to the fields of oncology, stem cell reprogramming and pharmacy. Particularly, it relates to a method for reprogramming (transdifferentiating) human tumor cells directly into non-oncogenic cells and apoptosis by multi-target induction using a small molecule composition, and the small molecule composition. The small molecule composition can be prepared into drugs or medical formulations in combination with pharmacologically acceptable carrier(s) or excipient(s), for use in, for example, clinical therapy of tumors. The small molecule compositions can also be prepared into reagents or cultural media with addition of aqueous or organic solvent(s), a basal medium, or a serum-free medium.

TECHNICAL BACKGROUND

According to the World Health Organization, about 14.1 million new cancer cases and 8.2 million deaths occurred in 2012 worldwide ("Global Cancer Statistics, 2012", CA Cancer). In China, there were 3.37 million cancer cases and 2.11 million cancer deaths recorded in 2011, which means every minute, 6.4 people were diagnosed with cancer and 5 people died from cancer. Lung cancer ranks the first in mortality, followed by cancers of liver, stomach, esophagus and colorectum. Liver cancer has the lowest five-year survival rate, 10.1%, and lung cancer was the next, 16.1% ("Cancer statistics in China, 2015"). The incidence rate of tumor is rising year by year.

Tumors are composed of various abnormal cells at different degrees of differentiation, and characterized by heterogeneity. Current anti-tumor therapies, including radiotherapy, chemotherapy, targeted therapy, immune-biological therapy, induction of differentiation and killing and the like, are directed to killing of tumor cells, which is however clinically demonstrated as incapable of overcoming tumor heterogeneity. Moreover, these therapies are found struggling with limited therapeutic efficacy, significant toxicity, drug resistance, high recurrence rate, and low five-year survival rate. Accordingly, there is such a long-existing need for a novel anti-tumor drug having high efficacy and low toxicity to provide a new approach of anti-tumor therapy and to improve patient survival.

The basic idea proposed herein is to transdifferentiate tumor cells directly into normal or non-oncogenic cells, instead of killing them, whereby a novel therapeutic process that can overcome tumor heterogeneity with high efficacy and low toxicity is provided.

Cell reprogramming is a process in which cells are converted from one type to another by regulating cellular signaling pathways and epigenetic modification. The term "cell reprogramming" used herein mainly refers to induction of cell reprogramming and induced cell reprogramming. Cell reprogramming includes induced reprogramming of induced pluripotent stem cells (iPSCs) and direct reprogramming of cells (transdifferentiation), which has been widely used in transformation of normal types of cells. Reprogramming of certain tumor cells into iPSCs (oncogenicity maintained) by exogenous transcription factors has also been reported. The method provided herein induces and regulates tumor cells to be reprogrammed (transdifferentiated) directly into non-oncogenic cells, which is accompanied by apoptosis of tumor cells using small molecule compositions instead of transcription factors. This has never been reported.

SUMMARY

An object of the disclosure is to provide a small molecule composition and a method using same for multi-target induction of reprogramming (transdifferentiation) directly into non-oncogenic cells and accompanying tumor cell apoptosis in human tumor cells. The composition is also referred to as "small molecule composition inducing tumor cell transdifferentiation with apoptosis" herein below. The small molecule composition can be prepared into drugs or medical formulations by optionally combining with pharmacologically acceptable carrier(s) or excipient(s), for use in applications including clinical therapy of tumors. The small molecule composition can also be prepared into reagents or cultural media with addition of aqueous or organic solvent(s), a basal medium, or a serum-free medium.

The mechanism of the disclosure is largely defined, which includes: altered GSK3β and TGFβ signaling pathways in tumor cells under multi-target induction using a small molecule combination comprising a GSK3β inhibitor and a TGFβ inhibitor, optionally with a synergistic effect from a retinoid compound or other compound that induces epigenetic changes, induces changes in epigenetic regulation and expression profile in tumor cells, whereby the tumor cells transdifferentiate into non-oncogenic cells, which is accompanied by apoptosis in non-transdifferentiated tumor cells. In tumor cells of certain types, for a better effect, a BMP inhibitor can also be used to induce and regulate BMP signaling pathway, or BrdU or EdU. It should be noted that GSK3β inhibitors and TGFβ inhibitors include various combinations between two classes of small molecules, wherein each class includes molecules having the same function or targeting the same induction site(s), which are all capable of inducing transdifferentiation of tumor cells accompanied by tumor cell apoptosis of different degrees. The same applies to BMP inhibitors and retinoids. Accordingly, in addition to the specific exemplary embodiments described herein, combinations comprising various small molecules from each class that have the same function or targeting the same induction site(s), producing equal effect on the same signaling pathway, and combinations comprising various small molecules that can induce and regulate tumor cells to transdifferentiate directly into non-oncogenic cells. These combinations all fall within the scope of the invention.

Tumor cells are commonly "oncogenic" or characterized by "oncogenicity". By using the mechanism of the disclosure, hepatoma carcinoma cells, which are deemed as most heterogeneous tumor cells, are transdifferentiated into non-oncogenic cells. Based on this, various tumor or tumor cells, as represented by, for example, pancreatic cancer, lung cancer, gastric cancer, breast cancer, lymphoma, glioma have been transdifferentiated into non-oncogenic cells under chemical induction, which is accompanied by apoptosis in tumor cells. Therefore, the methods and the compositions described herein can be used against tumors of various types (such as live cancer) and tumor cells derived therefrom. That is, the methods and the compositions cause transdifferentiation of various tumor cells into non-oncogenic cells, which is accompanied by tumor cell apoptosis of different degrees.

In a first aspect, the disclosure provides a small molecule composition (or a formulation) for chemically inducing human tumor cells to be reprogrammed and transformed or transdifferentiated directly into non-oncogenic cells and accompanying tumor cell apoptosis, wherein the composition comprises a GSK3β inhibitor and a TGFβ inhibitor, or the composition consists of a GSK3β inhibitor and a TGFβ inhibitor.

In a preferred embodiment, the composition comprises:
A GSK3β inhibitor: 0.046-4.65 parts by weight; and
A TGFβ inhibitor: 0.038-7.68 parts by weight.

In another preferred embodiment, the composition can be a solution and comprises:
A GSK3β inhibitor: a final concentration of 0.1-10 μM; and
A TGFβ inhibitor: a final concentration of 0.1-20 μM.

In another preferred embodiment, the composition comprises:
A GSK3β inhibitor: 0.232-2.325 parts by weight; and
A TGFβ inhibitor: 0.192-3.84 parts by weight.

In another preferred embodiment, the composition can be a solution and comprises:
A GSK3β inhibitor: a final concentration of 0.5-5 μM; and
A TGFβ inhibitor: a final concentration of 0.5-10 μM.

In another preferred embodiment, based on the total weight of the composition, the GSK3β inhibitor and the TGFβ inhibitor sum to 0.01-99.9% by weight; or, for example, 0.1-50% by weight (e.g., in a solution) or 50-99.9% by weight; or more specifically, 1%, 5%, 10%, 20%, 30%, etc.

In another preferred embodiment, in the composition described herein, the GSK3β inhibitor (or GSK3β inhibitor CHIR99021) and the TGFβ inhibitor (or TGFβ inhibitor SB431542 or/and A83-01) are present at a weight ratio of (0.046-4.65):(0.038-7.68); preferably, (0.232-2.325):(0.192-3.84); or, at a molar ratio of (0.1-10):(0.1-20) in a solution; preferably (0.5-5):(0.5-10).

In another preferred embodiment, the composition comprises:
A retinoid compound: 0.03-6.0 parts by weight; preferably 0.15-3 parts by weight. The addition of a retinoid compound can facilitate and enhance the transdifferentiation and the accompanying apoptosis of tumor cells, or expand the applicable range of tumors.

In another preferred embodiment, the composition described herein can be a solution and comprises a retinoid compound at a final concentration of 0.1-20 μM, preferably 0.5-10 μM.

In another preferred embodiment, based on the total weight of the composition, the GSK3β inhibitor, the TGFβ inhibitor and the retinoid compound sum to 0.02~99.9% by weight, for example 0.2-50% or 50-99.9%, more specifically, such as 1%, 5%, 10%, 20%, 30%, 40%, etc.

In another preferred embodiment, in the composition described herein, the GSK3β inhibitor (or GSK3β inhibitor CHIR99021), the TGFβ inhibitor (or TGFβ inhibitor SB431542 or/and A83-01) and the retinoid compound (or retinoic acids) are present at a weight ratio of (0.046-4.65):(0.038-7.68):(0.03-6.0), preferably (0.232-2.325):(0.192-3.84):(0.15-3), or at a molar ratio of (0.1-10):(0.1-20):(0.1-20) in a solution, preferably (0.5-5):(0.5-10):(0.5-10).

In another preferred embodiment, the composition can include one or more of the components selected from the group consisting of:
A BMP inhibitor (such as LDN-193189): 0.02-4.65 parts by weight, preferably 0.203-2.03 parts by weight; or
BrdU: 0.15-30 parts by weight, preferably 1.5-15 parts by weight; or
EdU: 0.125-25 parts by weight, preferably 1.25-12.5 parts by weight.

In another preferred embodiment, the composition described herein can be in form of a solution and comprises one or more of the components selected from the group consisting of:
A BMP inhibitor, at a final concentration of 0.05-10 μM, preferably 0.5-5 μM;
BrdU, at a final concentration of 0.5-100 μM, preferably 5-50 μM; or
EdU, at a final concentration of 0.5-100 μM, preferably 5-50 μM.

The addition of a BMP inhibitor (such as LDN-193189), BrdU or EdU, can further facilitate or enhance the transdifferentiation and accompanying apoptosis in some malignant tumor cells.

In another preferred embodiment, based on the total weight of the composition, the GSK3β inhibitor, the TGFβ inhibitor, the retinoid compound, and/or the BMP inhibitor, and/or BrdU (or/and EdU) sum to 0.02-99.9% by weight, for example, 0.2-50% or 50-99.9%, more specifically, 1%, 5%, 10%, 20%, 30%, 40%, etc.

In another preferred embodiment, in the composition described herein, the GSK3β inhibitor (such as GSK3β inhibitor CHIR99021), the TGFβ inhibitor (such as TGFβ inhibitor SB431542 or/and A83-01), the retinoid compound (such as retinoic acids), the BMP inhibitor (such as BMP inhibitor LDN-193189) and BrdU are present at a weight ratio of: (0.046-4.65):(0.038-7.68):(0.03-6.0):(0.02-4.65):0.15-30, preferably (0.232-2.325):(0.192-3.84):(0.15-3):(0.203-2.03):(1.5-15), or at a molar weight of (0.1-10):(0.1-20):(0.1-20):(0.05-10):(0.5-100) in a solution, preferably, (0.5-5):(0.5-10):(0.5-10):(0.5-5):(5-50).

In another preferred embodiment, in the composition described herein, the GSK3β inhibitor (such as GSK3β inhibitor CHIR99021), the TGFβ inhibitor (such as TGFβ inhibitor SB431542 or/and A83-01), the retinoid compound (such as retinoic acids), the BMP inhibitor (such as BMP inhibitor LDN-193189) and EdU are present at a weight ratio of (0.046-4.65):(0.038-7.68):(0.03-6.0):(0.02-4.65):(0.125-25), preferably (0.232-2.325):(0.192-3.84):(0.15-3):(0.203-2.03):(1.25-12.5), or at a molar ratio of (0.1-10):(0.1-20):(0.1-20):(0.05-10):(0.5-100) in a solution, preferably, (0.5-5):(0.5-10):(0.5-10):(0.5-5):(5-50).

For the weight ratios described herein, the unit of weight can be any of kilogram (kg), milligram (mg), microgram (μg); for the molar ratios described herein, the molar unit can be any of mole (M), millimole (mM), micromole (μM).

For large animals or human beings having tumor, the composition described herein can be applied in an effective dose calculated and converted based on doses designed for small animals (for example, by using solid-based or solution-based dose conversion), which also falls within the scope of the disclosure.

In another preferred embodiment, the GSK3β inhibitors include but are not limited to: GSK3β signaling pathway inhibitors or compounds of the same class that have the same function or target the same induction site(s), as represented by CHIR-99021, BIO, IM-12, TWS119, 1-Azakenpaullone, CHIR-98014, Tideglusib, AR-A014418, LY2090314, SB216763, AZD1080, or functionally equivalent pharmaceutical preparations, analogues, isomers and/or salts, hydrates or precursors thereof, or a combination thereof; preferably GSK3β inhibitor CHIR-99021.

The TGFβ inhibitors described herein include but are not limited to: TGFβ signaling pathway inhibitors or compounds of the same class that have the same function or target the same induction site(s), as represented by SB431542, A83-01, SB525334, LY2109761, RepSox, SD-208, GW788388, SB505124, EW-7197, or functionally equivalent pharmaceutical preparations, analogues, isomers and/or salts, hydrates or precursors thereof, or a combination thereof; preferably TGFβ inhibitor SB431542 or/and A83-01.

The retinoids described herein can be naturally occurring or artificially synthesized ones, including but not limited to: retinoid differentiation-inducing agents or compounds of the same class that have the same function or target the same induction site(s), as represented by retinoic acid (also referred to as all-transretinoic acid, ATRA), 13-cis retinoic acid, 9-cis retinoic acid, isotretinoin, etc., or functionally equivalent pharmaceutical preparations, analogues, isomers and/or salts, hydrates or precursors thereof, or a combination thereof; preferably retinoic acid (RA).

The BMP inhibitors described herein include but are not limited to: BMP signaling pathway inhibitors or compounds of the same class that have the same function or target the same induction site(s), as represented by LDN-193189, K02288, DMH1, etc., or functionally equivalent pharmaceutical preparations, analogues, isomers and/or salts, hydrates or precursors thereof, or a combination thereof; preferably, BMP inhibitor LDN-193189.

In another preferred embodiment, the composition described herein is a pharmaceutical composition and can further comprise a pharmaceutically acceptable carrier or excipient, where the carrier or excipient includes (but is not limited to): water, saline, phosphate buffer, or other aqueous solvents; DMSO (dimethyl sulfoxide), glycerin, and ethanol, or other organic solvents; microspheres, liposomes, microemulsions, or polymeric surfactants; colloidal drug delivery systems or polymer drug delivery systems; or preservatives, antioxidants, flavoring agents, fragrances, solubilizers, emulsifiers, pH buffers, adhesives, fillers, lubricants, or other pharmaceutical excipients.

In another preferred embodiment, the composition described herein can be prepared into a dosage forms including (but is not limited to): solid dosage forms, including (but not limited to): powders, pulvis, tablets, pills, capsules, sustained release formulations, controlled-release formulations; liquid dosage forms, including (but not limited to) injections, infusions, suspensions, or other liquid dosage forms; gaseous dosage forms; or semi-solid dosage forms.

In another preferred embodiment, the composition described herein can further include an aqueous solvent or an organic solvent to form an agent useful in research, or be combined with a basal medium or a serum-free medium to form a medium for inducing tumor cells to be reprogrammed directly into non-oncogenic cells. Particularly, components of the composition are present in a basal cell culture medium containing 5-20% of calf serum, 1% of penicillin-streptomycin mix (100×) or a serum-free medium containing various cytokines or growth factors. The composition does not include basal medium for cell differentiation.

In another aspect, the disclosure provides use of the composition described herein for developing or preparing anti-tumor drugs (or pharmaceutical formulations), or for preparing media or agents for inducing human tumor cells to be reprogrammed (transdifferentiated) directly into non-oncogenic cells, which is accompanied by tumor cell apoptosis.

In another aspect, the disclosure provides a method for inducing tumor cells to be reprogrammed directly into non-oncogenic cells, which is accompanied by tumor cell apoptosis, wherein the steps include: inducing and regulating human tumor cells to be transdifferentiated directly into non-oncogenic cells, which is accompanied by apoptosis of the tumor cells, by using the composition of any of claims 1-6.

In another preferred embodiment, provided is a method of preparing the medium or agent for inducing the transdifferentiation of human tumor cells with apoptosis, including:

(1) Preparation of concentrated solution: dissolving each of the components of the composition of any of claims 1-6 in an organic solvent or an aqueous solvent to obtain a concentrated solution; preferably, the organic solvent includes dimethylsulfoxide; and preferably, the aqueous solvent includes water, normal saline, phosphate buffer.

(2) Formulation of medium: diluting the concentrated solution of step (1) in a basal cell culture medium containing 5-20% calf serum and 1% penicillin-streptomycin mix (100×) or a serum-free medium containing various cytokines or growth factors, (so that each of the components has a concentration as defined for the composition of any of claims 1-6) to produce a medium for inducing the transdifferentiation accompanied by apoptosis of tumor cells; in which the percentage content for each component in the medium can vary with a range of ±50%, preferably ±30% preferably ±20%, for example ±10%, ±5% of the specified value.

(3) Induction of transdifferentiation accompanied by apoptosis of tumor cells: suspending the tumor cells in the medium formulated in step (2) for inducing the transdifferentiation accompanied by apoptosis of tumor cells, and plating the suspension to prepare a treatment group; adding the solvent that is used in the treatment group (such as DMSO or other solvents) into the basal cell culture medium containing 10% calf serum, 1% penicillin-streptomycin mix (100×) (or the serum-free medium containing various cytokines or growth factors) that is used in the treatment group to prepare a "control medium" (percentages all refer to "% (v/v)"); then adding and suspending tumor cells in the same number as in treatment group into the "control medium" and plating to prepare a control group; culturing the cells at 37° C., with the medium changed every 2-4 days and cells subcultured every 3-7 days.

(4) Continuous passage culture inducing transdifferentiation accompanied by apoptosis of tumor cells: discarding the original culture medium, washing the cells once with PBS, adding a digestion solution for cell digestion at 37° C. for 1-5 minutes; stopping the cell digestion, centrifuging the cells and discarding the supernatant, resuspending cell pellet and plating at a ratio of 1:1-1:3; culturing the cells according to steps (1) and (2), with medium changed every 2-4 days and cells subcultured every 3-7 days; the digestion solution comprises trypsin, EDTA, Acutase, TrypleE, etc.

(5) Induction of transdifferentiation accompanied by apoptosis of tumor cells to obtain normal or non-oncogenic cells: continuous passage culturing the tumor cells according to steps (3) and (4) for transdifferentiaton accompanied by apoptosis for 1-4 weeks, washing off the apoptotic cells with PBS to obtain the transdifferentiated non-oncogenic cells.

In another aspect of the disclosure, provided is a kit for inducing human tumor cells to reprogrammed directly into non-oncogenic cells accompanied by tumor cell apoptosis, which comprises a composition described herein, or an anti-tumor drug or pharmaceutical formulation developed and prepared based on the composition, or an agent or medium that is developed and prepared based on the composition.

The tumors or tumor cells include but are not limited to: liver cancer, lung cancer, stomach cancer, colorectal cancer, pancreatic cancer, breast cancer, ovarian cancer, prostate cancer, osteosarcoma, lymphoma, leukemia, nasopharyngeal cancer, esophageal cancer, cervical cancer, oral cavity cancer, salivary gland tumor, nasal cavity and paranasal cavity sinus malignant tumor, laryngeal cancer, otic tumor, ocular tumor, thyroid tumor, mediastinal tumor, thoracic wall and pleural tumor, intestinal tumor, biliary tract tumor, pancreatic and periampullary tumor, mesenteric and retroperitoneal tumor, renal tumor, adrenal tumor, bladder tumor, testicular tumor, penile cancer, endometrial cancer, ovarian malignant tumor, malignant trophoblastic tumor, vulvar and vaginal cancer, malignant lymphoma, multiple myeloma, soft tissue tumor, bone tumor, skin and adnexal tumor, malignant melanoma or nervous system tumors and other hematological and solid tumors or cells thereof; preferably liver cancer or hepatoma cells.

Based on the disclosure, other aspects of the invention will be readily apparent to the skilled artisan.

A: Hepatoma cells SMMC-7721 induced and transdifferentiated into non-oncogenic hepatocyte-like cells after being cultured for 10 days in Medium 6, as evidenced by substantial change in morphology;

B: Apoptosis statistics of hepatoma cells SMMC-7721 cultured using Medium 6 for induced transdifferentiation accompanied by apoptosis for 1-14 days.

Blue columns correspond to early apoptosis (Early); red columns correspond to late apoptosis (Late); T, T1W, T2W correspond to the apoptosis of hepatoma cells SMMC-7721 immediately after treatment, 1 week after treatment and 2 weeks after treatment, respectively. Apoptosis results show statistically significant difference between the control group and the treatment group ($p<0.05$).

Figure 2:
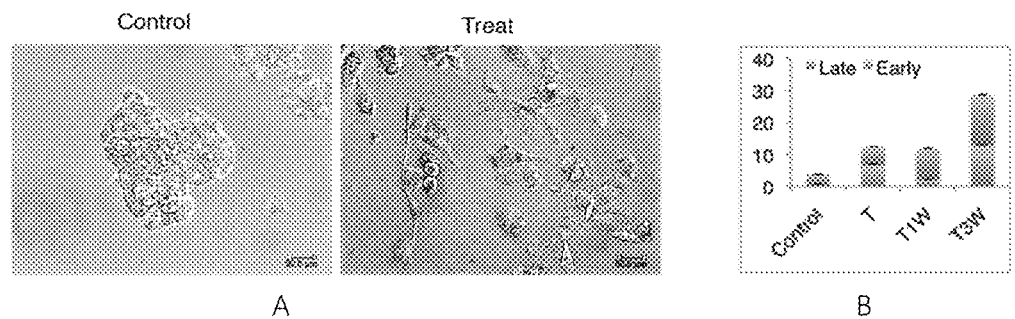

FIG. 2. Induced transdifferentiation of hepatoma cells HepG2 and accompanying apoptosis by using Media 4, and 1.

A: hepatoma cells HepG2 induced and transdifferentiated into non-oncogenic hepatocyte-like cells by culturing in Medium 4 for 8 days, as evidenced by substantial change in morphology;

B: hepatoma cells HepG2 induced and transdifferentiated using Medium 1, and accompanying apoptosis.

Blue columns correspond to early apoptosis (Early); red columns correspond to late apoptosis (Late); T, T1W, T3W correspond to the apoptosis states of the cells immediately after treatment, 1 week after treatment and 3 weeks after treatment, respectively. Apoptosis results show statistically significant difference between the control group and the treatment group ($p<0.05$).

Figure 3:
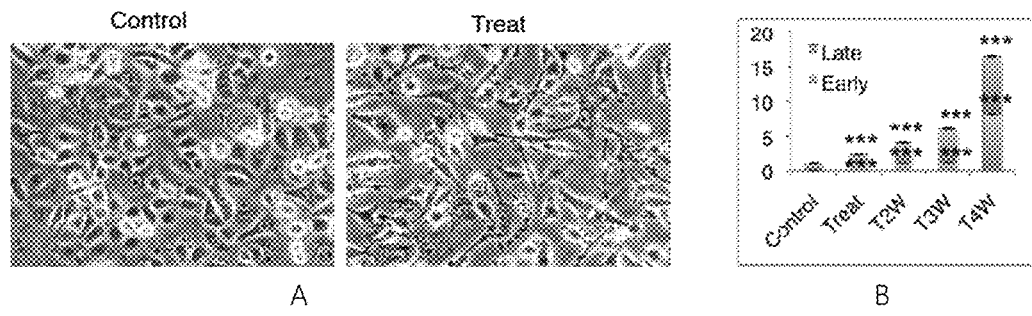

FIG. 3. 5-Fu-resistant hepatoma cells 7402/5-Fu induced and transdifferentiated (with accompanying apoptosis) using Media 5 and 2.

A: hepatoma cells 7402/5-Fu in the treatment group (on the right) induced and transdifferentiated using Medium 5, as evidenced by substantial change in morphology;

B: hepatoma cells 7402/5-Fu induced and transdifferentiated using Medium 2, and accompanying apoptosis. Blue columns correspond to early apoptosis (Early); red columns correspond to late apoptosis (Late); T2W, T3W, T4W correspond to the apoptosis states of the cells 2 weeks after treatment, 3 weeks after treatment and 4 weeks after treatment, respectively. Apoptosis results show statistically significant difference between the control group and the treatment group ($p<0.05$).

Figure 4:
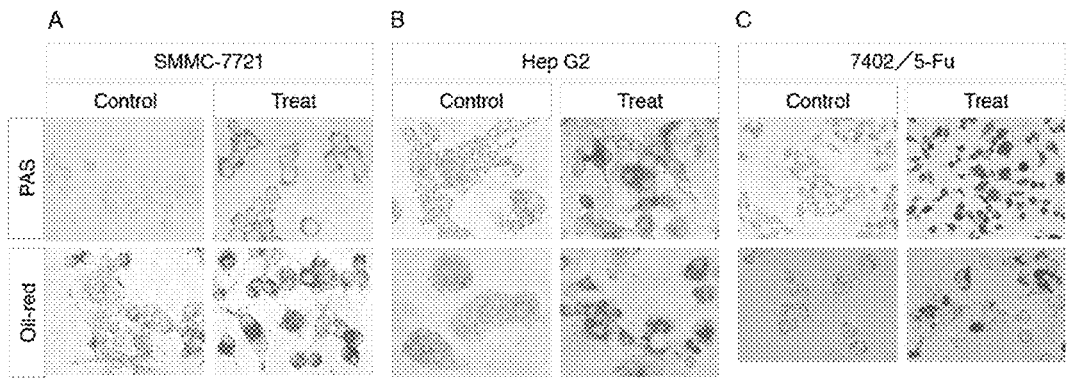

FIG. 4. Hepatoma cells SMMC-7721 (Medium 6), HepG2 (Medium 4), 7402/5-Fu (Medium 5) induced and transdifferentiated into non-oncogenic hepatocyte-like cells as functional as normal hepatocytes. PAS: glycogen staining, Oil-red: oil-red staining, reflecting fat uptake.

Figure 5:
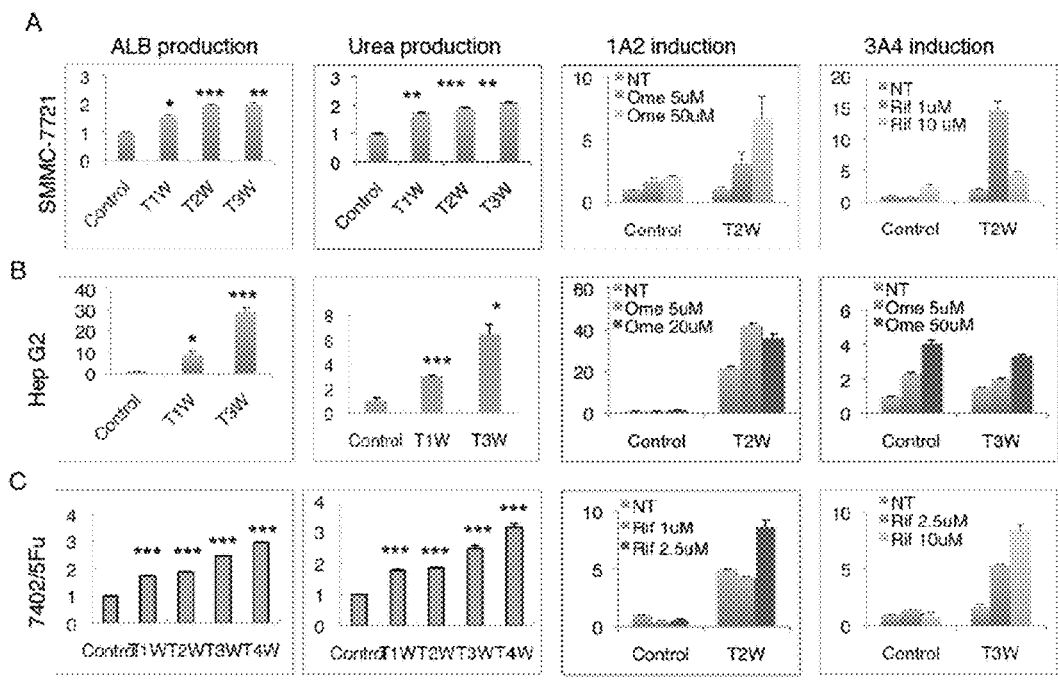

FIG. 5. Hepatoma cells SMMC-7721 (Medium 10), HepG2 (Medium 11), 7402/5-Fu (Medium 12) induced and transdifferentiated into non-oncogenic hepatocyte-like cells as functional as normal hepatocytes in terms of albumin secretion (ALB), urea production (Urea), CYP1A2 induction and CYP3A4 induction.

A. Non-oncogenic hepatocyte-like cells obtained from induced transdifferentiation of hepatoma cells SMMC-7721 using Medium 10, functional as normal hepatocytes;

B. Non-oncogenic hepatocyte-like cells obtained from induced transdifferentiation of hepatoma cells HepG2 using Medium 11, functional as normal hepatocytes;

C. Non-oncogenic hepatocyte-like cells obtained from induced transdifferentiation of 5-Fu resistant hepatoma cells 7402/5-Fu using Medium 12, functional as normal hepatocytes;

T1W, T2W, T3W refer to 1-week, 2-week, and 3-week treatments, respectively. Rif: Rifampicin; Ome: Omeprazole.

Figure 6:
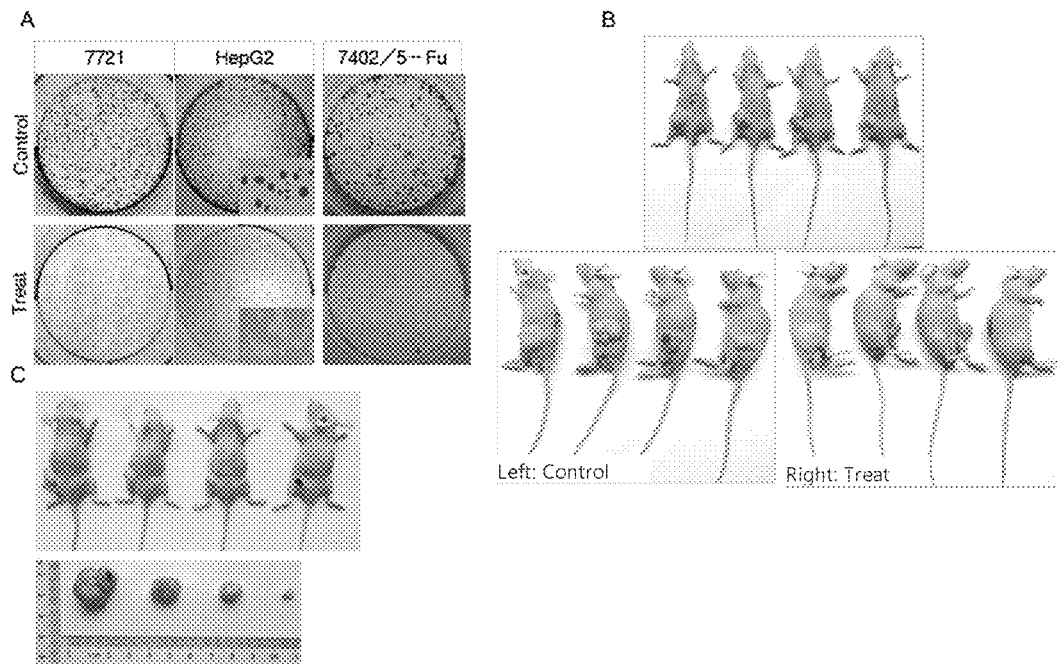

FIG. 6. The non-oncogenic hepatocyte-like cell obtained by the induced transdifferentiation of hepatoma cells SMMC-7721 (Medium 6), HepG2 (Medium 4) and 7402/5-Fu (Medium 5) exhibiting loss of oncogenicity in vitro and in vivo.

A: The non-oncogenic hepatocyte-like cells obtained by the induced transdifferentiation of hepatoma cells SMMC-7721, HepG2 and 7402/5-Fu using Media 6, 4, 5 cultured in vitro showed no colony formation and lost oncogenicity;

B: The non-oncogenic hepatocyte-like cells obtained by the induced transdifferentiation of hepatoma cells SMMC-7721 showed no tumor formation in vivo (treated for 4 weeks) and lost oncogenicity in vivo (Medium 6).

C: The non-oncogenic hepatocyte-like cells obtained by the induced transdifferentiation of hepatocellular carcinoma 7402/5-Fu showed no tumor formation in vivo (treated for 4 weeks) and lost oncogenicity in vivo (Medium 5); Top image: cells from the treatment group did not show tumor formation in hind leg (right lateral) and lost oncogenicity; cells from the control group showed tumor formation; Bottom image: anatomic appearance of the tumors formed from the control group.

Figure 7:
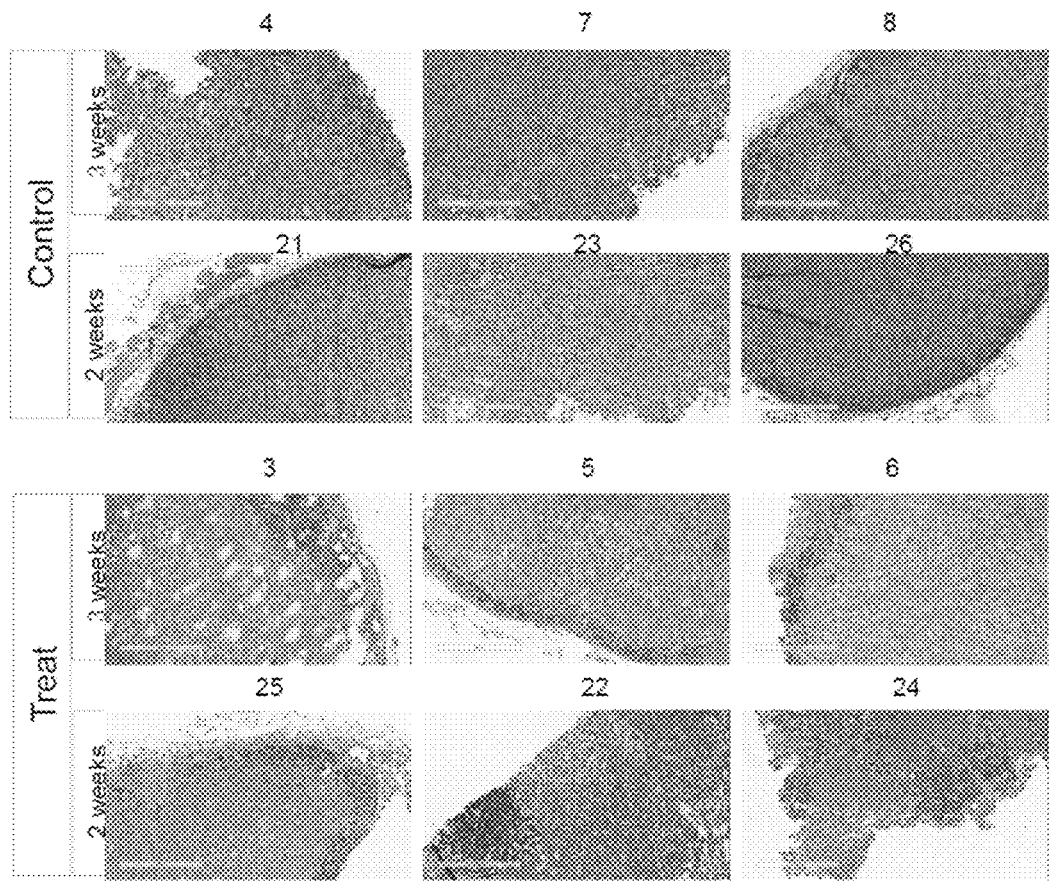

FIG. 7. Assay of patient's hepatoma tissue in PDX animal model—in vivo application of the small molecule combination (Composition 8 for transdifferentiation with accompanying apoptosis). Results showed that tissue necrosis, structural disruption or loss was observed (stained red) in tumor tissues from the treatment group; no change in cellular structure was observed in tumor tissues (stained purple) (PDX-80872) from the control group. Numbers 4, 7, 8 represent the codes on mouse ear tags.

Figure 8:
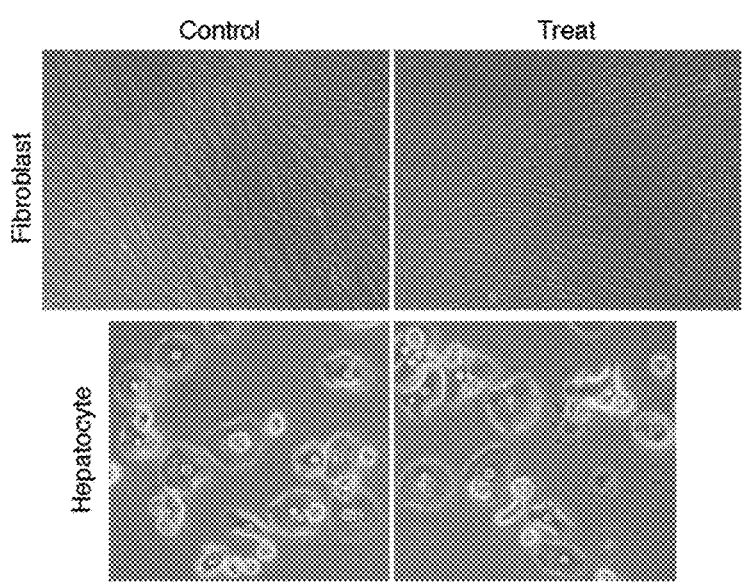

FIG. 8. No morphometric change was observed in normal human fibroblasts and hepatocytes treated (transdifferentiated with accompanying apoptosis, using Medium 8, 3) for 3 weeks, suggesting no influence.

Figure 9:
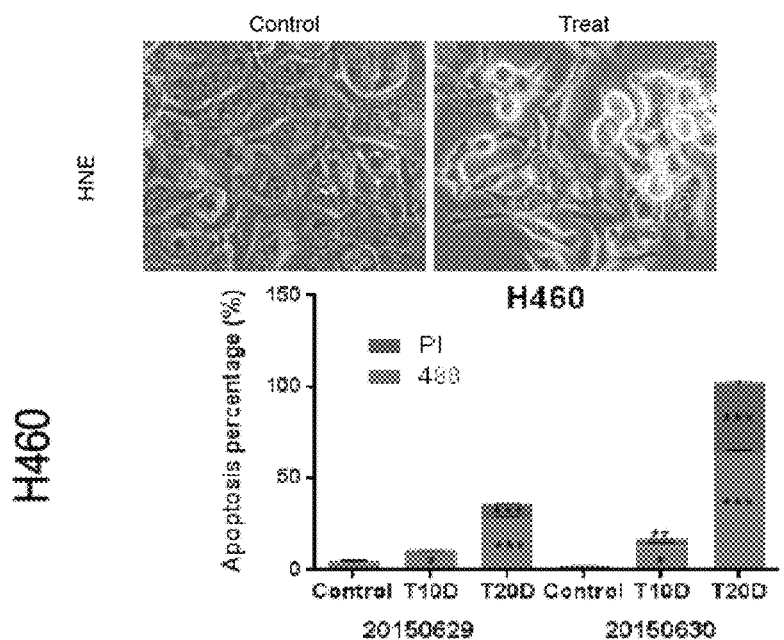

FIG. 9. Nasopharyngeal carcinoma cells HNE and lung carcinoma cells H460 were induced and transdifferentiated using Medium 9 and 7, respectively, with accompanying apoptosis. As can be seen in FIG. 9, the cancer cells from the treatment group of nasopharyngeal carcinoma cells HNE (treated using Medium 9) showed totally changed morphology after transdifferentiation, suggesting that the cells were transdifferentiated; the cancer cells from the treatment group of lung carcinoma cells H460 were treated (using Medium 9 and 7, respectively), in which almost all of the lung carcinoma cells H460 were induced to apoptosis using Medium 7 (in this Figure, green columns correspond to early apoptosis, red column for late apoptosis; T10D, T20D refer to 10-day and 20-day treatments, respectively); while lung carcinoma cells H460 from control group showed almost no apoptosis.

Figure 10:
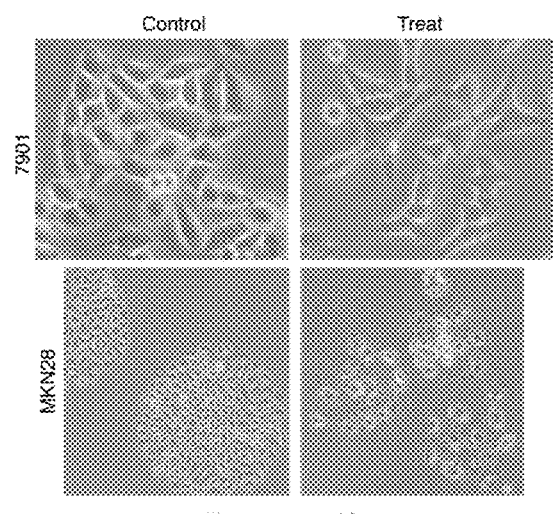

FIG. 10. Gastric cancer cells SGC-7901 and MKN28 were induced and transdifferentiated using Media 12 and 13 for 2 weeks. Gastric cancer cells SGC-7901 (Medium 12) and MKN28 (Medium 13) were each treated for 2 weeks. Cancer cells from the treatment group showed totally changed morphology after the treatment, suggesting that the cells were transdifferentiated.

Figure 11:
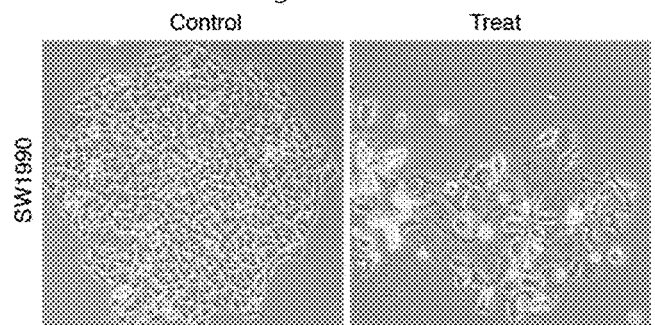

FIG. 11. Pancreatic cancer cells SW1990 were induced and transdifferentiated using Medium 12 for 2 weeks). Cancer cells from the treatment group of pancreatic cancer cells SW1990 showed totally changed morphology after the treatment, suggesting that the cells were transdifferentiated.

Figure 12:
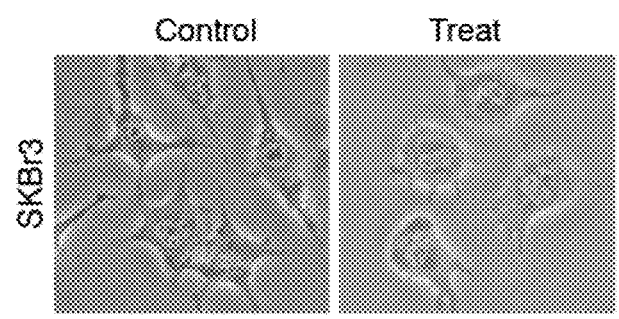

FIG. 12. Breast cancer cells SKBr3 were induced and transdifferentiated using Medium 13 for 2 weeks. Cancer cells from treatment group of breast cancer cells SKBr3 showed totally changed morphology after the treatment, suggesting that the cells were transdifferentiated.

Figure 13:
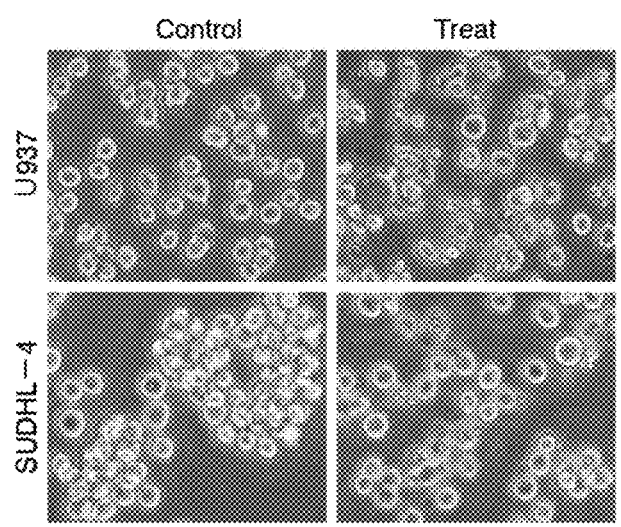

FIG. 13. Leukemia cells U937, B cell lymphoma SUDHL-4 were induced and transdifferentiated (with apoptosis) using Media 10, 11 for 10 days. Most of the cancer cells from the treatment groups of Leukemia cells U937 (Medium 10) and B cell lymphoma SUDHL-4 (Medium 11) showed induced apoptosis and loss of integrity in morphology.

Figure 14:
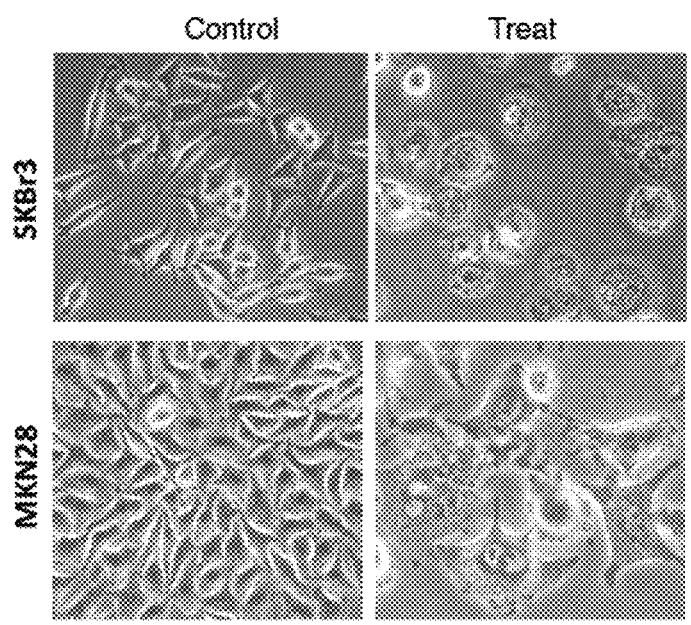

FIG. 14. Breast cancer cells SKBr3 and gastric cancer cells MKN28 were induced and transdifferented using Media 13 and 14. Breast cancer cells SKBr3 and gastric cancer cells MKN28 were treated using Media 13, 14 for 2 weeks. Top and bottom images on the right side show that cancer cells from the treatment group (T) had totally changed morphology, suggesting that the cells were transdifferentiated.

Figure 15:
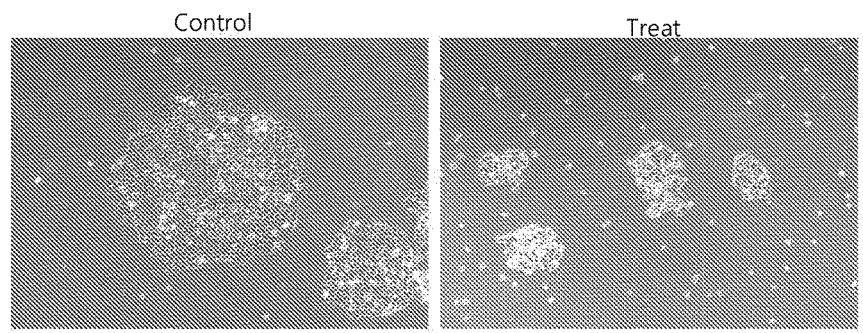

FIG. 15. Intestinal cancer HCT116 cells lost oncogenicity after induced transdifferentiation using small molecule composition. Intestinal cancer cells HCT116 were treated using Medium 9 for 2 weeks. Right: Cells from the treatment group of intestinal carcinoma cells HCT116 showed totally changed morphology, with no more colony formed, suggesting that the cells were transdifferentiated and lost oncogenicity.

Figure 16:
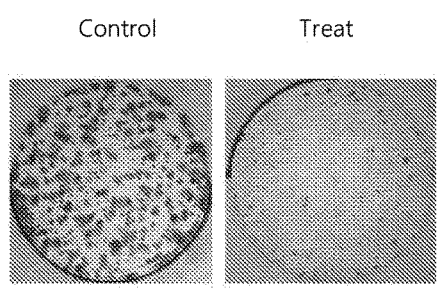

FIG. 16. Prostatic carcinoma PC-3 cells lost oncogenicity after induced transdifferentiation using small molecules. Prostatic carcinoma PC-3 cells were treated using Medium 5 for 2 weeks. Right: Pancreatic carcinoma PC-3 cells did not show colony formation after the induced transdifferentiation, and lost oncogenicity in vitro.

Figure 17:
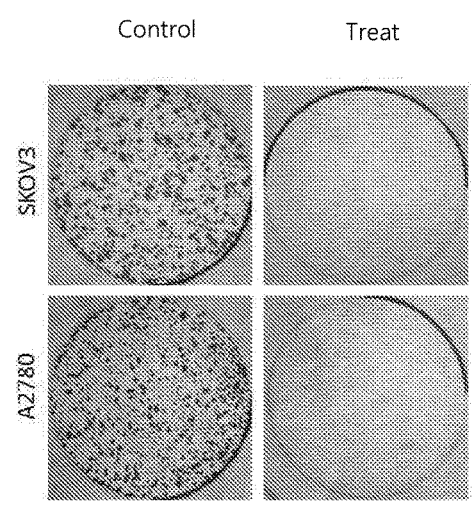

FIG. 17. Ovarian carcinoma cells SKOV3 and A2780 cells lost oncogenicity after induced transdifferentiation using small molecules. Top and bottom images on the right side: Ovarian carcinoma cells SKOV3 and A2780 in the treatment groups did not show colony formation after the transdifferentiation induced using Media 7, 8, and lost oncogenicity.

Figure 18:
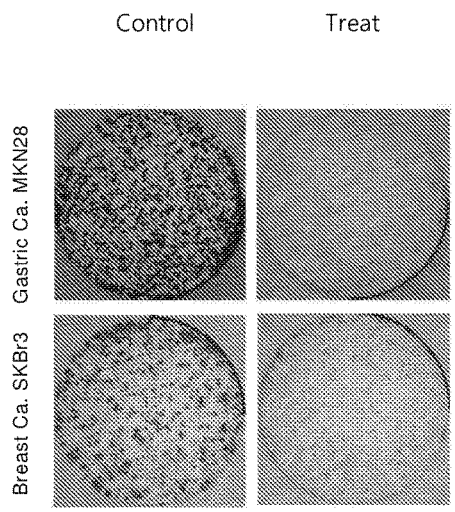

FIG. 18. Gastric carcinoma, breast carcinoma cells lost oncogenicity after transdifferentiation induced by small molecules. Top and bottom images on the right side: Gastric cancer cells MKN28 and breast carcinoma cells SKbr3 in treatment groups, which were treated using Media 10 and 11 respectively for 2 weeks, did not show colony formation after the induced transdifferentiation and lost oncogenicity.

Figure 19:
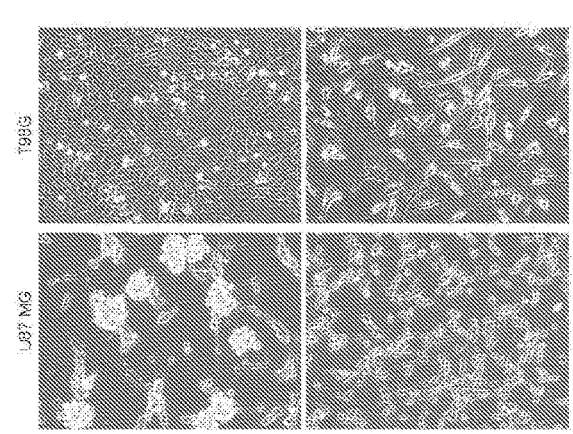

FIG. 19. Glioma cells showed totally changed morphology after transdifferentiation induced by small molecules. Top and bottom images on the right side: Glioma cells T98G and U87MG, which were treated using Media 4 and 5 respectively for 2 weeks, showed totally changed morphology after the induction, suggesting that the cells were transdifferentiated.

Figure 20:
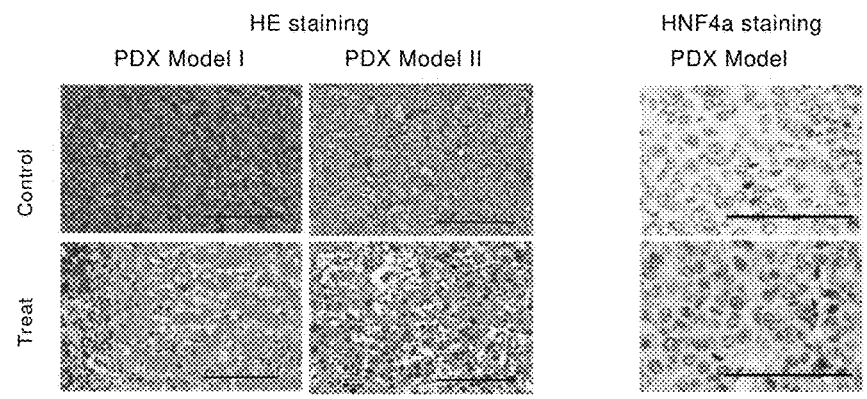

FIG. 20. In vivo assay in hepatoma PDX animal model using small molecule combination. Left: liver cancer tissues and cells in the treatment group, which were treated using Injection 21 formulated using "transdifferentiation and accompanied apoptosis small molecule composition 21" for 3 weeks, showed massive necrosis and disrupted or lost cancerous structure. Right: the treatment groups showed that after being treated with the small molecule agent for 3 weeks, the remaining tissues and cells exhibited expression of human hepatocyte-specific marker HNF4a, suggesting that the cells were transdifferentiated.

Figure 21:
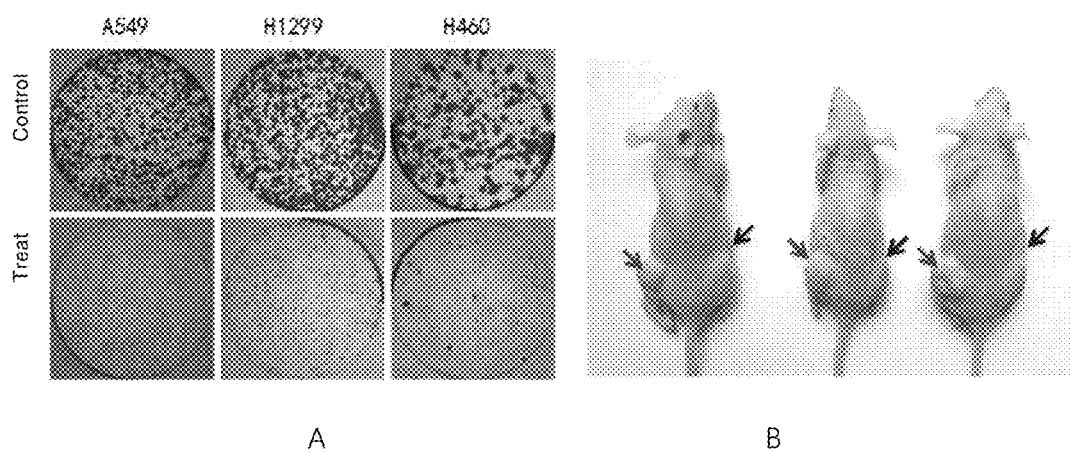

FIG. 21. Lung carcinoma cells lost oncogenicity in vitro and in vivo after the induced transdifferentiation using small molecules. A: results obtained using Medium for 2 weeks, in which the bottom images show that lung carcinoma cells A549, H1299 and H460 in the treatment groups treated using Media 14, 13 and 9 respectively did not form colony after the induced transdifferentiation and lost oncogenicity; B: the transdifferentiated lung carcinoma cells in treatment group were injected into right hind legs of nude mice (marked with blue arrows) and did not show tumor formation in 4 weeks, suggesting that the lung carcinoma cells A549 (treated with Medium 14) were induced and transdifferentiated and lost oncogenicity in vivo. The parts marked with red arrows show the tumors formed from the untreated lung carcinoma cells.

Figure 22:
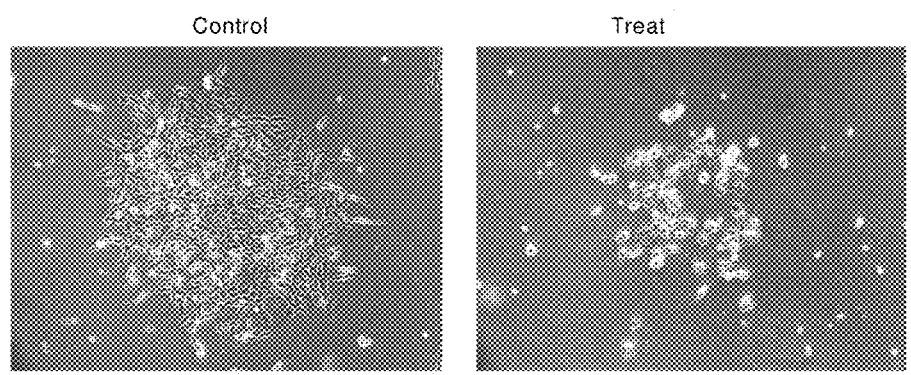

FIG. 22. Lung carcinoma cells H1299 lost oncogenicity in vitro after transdifferentiation using the small molecules. Right: lung carcinoma cells H1299 in the treatment group (treated using Medium 15 for 2 weeks) did not show colony after transdifferentiation and lost oncogenicity.

Figure 23:
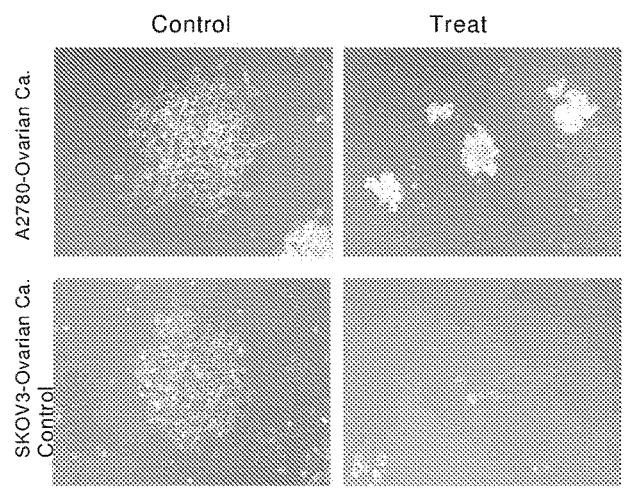

FIG. 23. Ovarian carcinoma cells A2780, SKOV3 lost oncogenicity in vitro after the induced transdifferentiation. Top and bottom images on the right: in the treatment groups, ovarian carcinoma cells A2780 and SKOV3 treated using Medium 16 and Medium 17 respectively for 2 weeks, were transdifferentiated, and lost colony-forming capability and oncogenicity.

Figure 24:
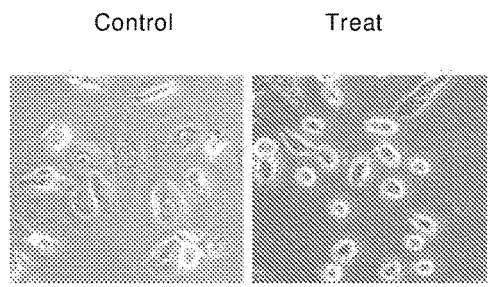

FIG. 24. After being treated using Medium 18 for 2 weeks, prostatic carcinoma cells PC9 were induced and transdifferentiated. Right: in the treatment group, prostatic carcinoma cells PC9 exhibited totally changed morphology after the induction, suggesting that the cells were transdifferentiated.

Figure 25:
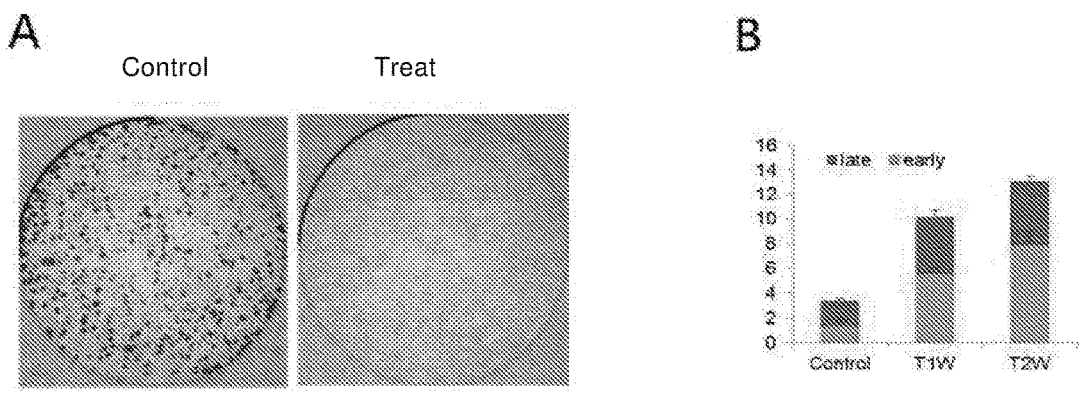

FIG. 25. Gastric carcinoma SGC-7901 cells were induced and transdifferentiated using Media 19 and 20 respectively. A: in the treatment group, gastric carcinoma SGC-7901 cells (treated using Medium 19 for 2 weeks) did not show colony formation after transdifferentiation and lost oncogenicity in vitro. B: statistics of induced apoptosis in gastric carcinoma SGC-7901 cells (treated with Medium 20 for 2 weeks). Green columns: early apoptosis (Early); Red columns: late apoptosis (Late); T1W, T2W: apoptosis statistics of 1-week and 2-week treatment; the control groups showed minimal early, late natural apoptosis; the control and the treatment groups had statistically significant difference in apoptosis results (p<0.005).

Figure 26:
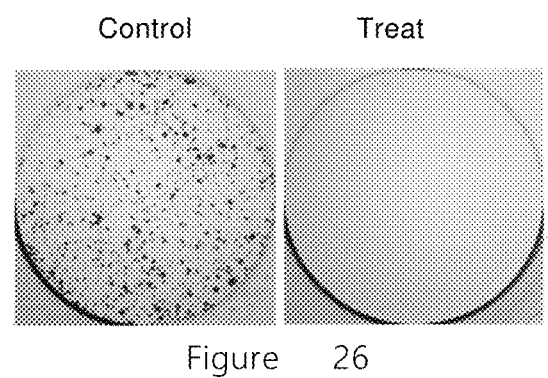

FIG. 26. Pancreatic carcinoma SW1990 cells lost oncogenicity after the induced transdifferentiation using Medium 16 for 2 weeks. Right: in the treatment group, the pancreatic carcinoma SW1990 cells did not show colony formation after transdifferentiation and lost oncogenicity in vitro.

DETAILED DESCRIPTION

The inventors provided a method of inducing human tumor cells to be reprogrammed (transdifferentiated) directly into non-oncogenic cells and accompanying apoptosis in tumor cells using a small molecule composition, and the small molecule composition. The small molecule compositions can be prepared into medications or medical formulations by optionally combining with pharmacologically acceptable carrier(s) or excipient(s) for use in, for example, clinical therapy of tumors. The small molecule compositions can also be prepared into reagents or cultural media with addition of aqueous or organic solvent(s), a basal medium, or a serum-free medium. The method of inducing human tumor cells to be reprogrammed (transdifferentiated) directly into non-oncogenic cells using the small molecule composition was first applied to hepatoma carcinoma cells, whereby the hepatoma carcinoma cells were transdifferentiated directly into non-oncogenic hepatocyte-like cells, which is accompanied by apoptosis of hepatoma carcinoma cells. The transdifferentiated hepatocyte-like cells showed normal functions as hepatocytes. No damage to normal hepatocytes and fibroblasts was observed so far. Based on this, by using the small molecule composition, various tumor or tumor cells from representative tumors such as lung cancer, gastric cancer, pancreatic cancer, breast cancer, leukemia, lymphoma, and glioma have been transdifferentiated into non-oncogenic cells, which is accompanied by apoptosis in tumor cells.

Basic Mechanism

By "chemically induced direct reprogramming (transdifferentiation) in cells", it means a process of altering the fate of cells by regulating cellular signaling pathway(s) and epigenetic regulation without change in genes.

With the development in stem cell science, research in cell reprogramming is innovating, from the achievement of reprogramming by introducing exogenous transcription factors, to the "chemical-induced reprogramming of induced pluripotent stem cells (iPSCs)" via regulation of cellular signaling pathway and epigenetics using small molecule combinations (Hongkui Deng et al., Pluripotent Stem Cells Induced from Mouse Somatic Cells by Small-Molecule Compounds. Science. 341,651-4, 2013) and "chemical-induced direct reprogramming of cells" (Li X, Zuo X, Jing J, Ma Y, Wang J, Liu D, Zhu J, Du X, Xiong L, Du Y, Xu J, Xiao X, Chai Z, Zhao, Y, Deng, H. Small-Molecule-Driven Direct Reprogramming of Mouse Fibroblasts into Functional Neurons. Cell Stem Cell. 17 (2): 195-203, 2015; Hu W et al., Direct Conversion of Normal and Alzheimer's Disease Human Fibroblasts into Neuronal Cells by Small Molecules. Cell Stem Cell. 17 (2): 204-212, 2015); the starting and targeting types of cell reprogramming have been developed from differentiated cells converting to pluripotent stem cells, to converting to another differentiated cells; even pluripotent cells with remained oncogenicity can be achieved via reprogramming by exogenously introducing transcription factors into abnormal cells (myxoma cells) (Zhang X, Cruz F D, Terry M, Remotti F and Matushansky I. Terminal differentiation and loss of tumorigenicity of humancancers via pluripotency-based reprogramming. Oncogene, 2, 2249-2260, 2013); therefore, it has become possible to reprogram tumor cells directly into non-oncogenic cells by using small molecules.

TABLE 1

Examples of reprograming from various starting cell types into the same cell type of interests.

| Starting cell | Reprogramming mode | Targeting cell |
|---|---|---|
| Fibroblasts, hepatocytes, neural stem cells, foreskin cells, keratinocytes, amniotic fluid cells, blood cells, endothelial cells, etc. | Induced pluripotent cell reprogramming | Induced pluripotent stem cells (iPSCs) |
| Fibroblasts, astrocytes, hepatocytes, perivascular cells | Induced direct cell reprogramming (transdifferentiation) | Neurons |

As can be seen from the reported reprogramming of normal differentiated cells of various types into cells of the same type (Table 1), the key point is not the starting cell type, but the combination of inducing factors that can construct and maintain the specific gene expression profile or biological behavior of the cells of interests, and that can overcome various "barriers" in the process of reprogramming in the starting cells.

Therefore, if the inducing factors or compounds that can over various "barriers", and construct and maintain the specific gene expression profile or biological behavior of the cells of interests, besides differentiated cells from different blastoderms, tumor cells can also be reprogrammed to change their life circle. According to this, it is theoretically feasible to explore combinations of small molecule and then use them to induce and regulate transdifferentiation of tumor cells into respective non-oncogenic cells (targeting cells) with such combinations, and to overcome the heterogeneity of tumor cells.

Hepatic carcinoma (liver cancer), known as the most heterogeneous cancer, was selected as for a breakthough by the invention. Combinations of small molecules that can construct and maintain the specific gene expression profile or biological behavior of normal (non-oncogenic) hepatocytes (targeting cells) and also overcome various "barriers" in the process of the transdifferentiation of hepatoma cells into normal hepatocytes were investigated, and a method was developed for inducing transdifferentiation into non-oncogenic hepatocytes accompanied by apoptosis of in hepatoma cells by using such combinations of small molecules. Such method provides the following advantages: (1) stability of small molecules, controllable acting time, dosage and combination mode, stable and reliable effect; (2) the transdifferentiated hepatocyte-like cells have functions of normal mature human hepatocytes and lost oncogenicity in vitro; (3) the method can provide a strong transdifferentiation of hepatoma cells and bring no damage to normal hepatocytes and fibroblasts; cytocidal agents are not required to assist the killing of tumor cells, thus avoiding indiscriminative killing and side effects on normal tissue cells; (4) no need to introduce exogenous genes or change the genome structure of the cells, thus providing improved safety and reliability by avoiding new carcinogenic risks caused by introduction of exogenous genes or any change in genes; (5) the chemically-induced direct reprogramming here does not involve reprogramming into iPSCs, thus avoiding carcinogenic risks caused by stem cells.

The effective control and treatment provided by the method on human hepatic carcinoma, which is complex in pathogenesis with high heterogeneity and lacks an effective therapy, has great significance. In addition, continued study has shown that such small molecule combination can induce direct reprogramming (transdifferentiation) accompanied by apoptosis in various tumors, including nasopharyngeal cancer, lung cancer, gastric cancer, colorectal cancer, pancreatic cancer, breast cancer, ovarian cancer, prostate cancer, osteosarcoma, lymphoma, leukemia, and other hematologic tumors and substantial tumor cells, into non-oncogenic cells, and the effects are consistent. Accordingly, abundant trials have been conducted, which demonstrate that the small molecule combinations designed by the inventors can induce reprogramming (transdifferentiation) of tumor cells directly into non-oncogenic cells and apoptosis in non-transdifferentiated tumor cells. The concept and strategy of this disclosure have been demonstrated to be successful and effective.

Pharmaceutical Compositions and Use Thereof

The inventors studied and discovered for the first time that tumor cells can be induced to transdifferentiate accompanied by apoptosis by inhibiting both GSK3β and TGFβ. Due to the heterogeneity of tumor cells between individuals and tumor cell strains, the proportion between tumor cells induced to transdifferention and those induced to apoptosis varies, with some in favor of transdifferentiation and some in favor of apoptosis. Simultaneous inhibition of both GSK3β and TGFβ signaling pathways leads to more apoptosis, with transdifferentiation being less complete.

It is found that inhibition of GSK3β and TGFβ signaling pathways in combination with retinoic acids (RAs) can facilitate the small molecule combinations to induce tumor cells to transdifferentiate into non-oncogenic cells, with certain degrees of accompanying apoptosis of tumor cells. If further in combination with down-regulation of BMP signaling pathway and/or BrdU (or/and EdU), the transdifferentiation and the accompanying apoptosis in more malignant tumor cells can be enhanced or promoted. Although different proportions between transdifferentiation and apoptosis can be produced by the small molecule combinations due to the heterogeneities among tumors, the consistent final effect is that tumor cells are induced and transdifferentiated into non-oncogenic cells, which is accompanied by apoptosis of tumor cells. Therefore, the small molecule combinations are expected to be developed into new drugs or pharmaceutical formulations for anti-tumor therapy; and they can also be prepared into culture media or agents for use in researches of chemically-induced reprogramming directly into non-oncogenic cells and accompanying apoptosis in tumor cells.

It will be understood that in addition to the specific GSK3β inhibitors, TGFβ inhibitors, BMP inhibitors exemplified in the Examples herein, other inhibitors that are capable of inhibiting GSK3β signaling pathway, TGFβ signaling pathway, BMP signaling pathway, and those of the same class that target and regulate the same induction site(s) or have the same function, are equally or similarly effective to achieve the same technical effect and are therefore encompassed and envisaged in the invention.

Likewise, in addition to the specific retinoic acids (RAs) and retinoids exemplified in the Examples herein, other retinoids having the same function or targeting and regulating the same induction site(s) are equally or similarly effective to achieve the same technical effect and are therefore encompassed and envisaged in the invention.

As used herein, the terms "comprising", "containing" or "including" include "consisting essentially of" and "consisting of".

As used herein, the term "consisting essentially of" means that in the composition, in addition to the necessary ingredients or essential components, minor ingredients and/or impurities that do not affect the active ingredient may be contained. For example, sweeteners may be included to improve taste, antioxidants to prevent oxidation, and similarly, other pharmaceutical additives, carriers, and excipients commonly used in the art may be included.

As used herein, the term "pharmaceutically acceptable" ingredients are substances that are suitable for use in humans and/or animals without undue adverse side effects (such as toxicity, irritation, and allergies), i.e. substances having a reasonable benefit/risk ratio; such as drug carriers or excipients commonly used in the field.

As used herein, the term "effective amount" refers to an amount that can be functional or active in humans and/or animals and acceptable to humans and/or animals.

In the term "pharmaceutically acceptable carrier or excipient" as used herein, the "carrier" refers to a system that changes the manner in which the drug enters the body and its distribution in the body, controls the release rate of the drug, and delivers the drug to the targeted organ. The drug carrier itself is not an essential active ingredient and there is no excessive toxicity after administration. Suitable carriers are well known to those of ordinary skill in the art, including but not limited to: water, saline, phosphate buffer and other aqueous solvents; DMSO (dimethyl sulfoxide), glycerin and ethanol, and other organic solvents; microspheres, liposomes, microemulsions, polymeric surfactants; colloidal drug delivery systems, new polymer drug delivery systems, new drug carriers, and other pharmaceutical carriers; the "excipient" refers to additives other than the main active(s) in pharmaceutical preparations and may also be referred to as auxiliary substances. Substances such as adhesive, fillers, disintegrants, lubricants in tablets; wine, vinegar, concoction, etc. in Chinese traditional medicines; ointment in semi-solid preparations, the matrix part in creams; preservatives in liquid preparations, antioxidants, flavoring agents, fragrances, solubilizers, emulsifiers, solubilizers, osmotic pressure regulators, colorants and the like can all be used as excipients.

The general requirements for excipients are that they are stable in nature, compatible with the main drug, do not produce side effects, and do not affect the therapeutic effect. They are resistant to deformation, desiccation and cracking, moulds, parasites in ambient environment. They are harmless to human and have no physiological activity. They do not act with the main active(s) chemically or physically to interfere detection or tests of the main active(s). Detailed discussion about pharmaceutically acceptable carriers or excipients can be found in Remington's Pharmaceutical Sciences (Mack Pub. Co., N.J. 1991). The carriers or excipients include but are not limited to: aqueous solutions such as water, saline, and phosphate buffers; organic solvents such as DMSO (dimethyl sulfoxide), glycerin, and ethanol;

microspheres, liposomes, microemulsions, and macromolecular surfactants; colloidal drug delivery systems, novel macromolecular drug delivery systems, novel drug carriers, and other pharmaceutical carriers; preservatives, antioxidants, flavorings, fragrances, solubilizers, emulsifiers, pH buffers, and adhesives, fillers, lubricants in tablets, and other pharmaceutical excipients.

In the term "pharmaceutical dosage form into which the composition can be prepared" as used herein, the "pharmaceutical dosage form" refers to a pharmaceutical application form prepared to meet the needs of therapeutic or prophylactic treatments, referred to as a pharmaceutical dosage form. The pharmaceutical dosage forms that can be prepared by any of the compositions of the present invention include, but are not limited to, powders, pulvis, tablets, pills, capsules, sustained release agents, controlled-release agents, and other solid dosage forms; injections, infusions, suspensions, and other liquid dosage forms, as well as other dosage forms such as gaseous formulations and semi-solid formulations.

As used herein, "part(s) by weight" or "portion(s) by weight" may be used interchangeably, and the parts by weight may be any fixed amount expressed in micrograms, milligrams, grams, or kilograms (e.g., 1 μg, 1 mg, 1 g, 2 g, 5 g, or kg, etc.). For example, a composition consisting of 1 part by weight of component a and 9 parts by weight of component b may be a combination of 1 gram of component a+9 grams of component b, or else 10 grams of component a+90 grams of component b etc. In the composition, the percentage of a certain component=(the number of parts by weight for the component/the sum of the parts by weight for all components)×100%. Therefore, in a composition consisting of 1 parts by weight of component a and 9 parts by weight of component b, the content of component a is 10%, and the content of component b is 90%.

Further, in the solution state, the above-mentioned "parts by weight" may also be converted into "moles", and the "ratios of parts by weight" may be converted into "molar ratios". The parts by weight ratio may be expressed in units of kilograms (kg), milligrams (mg), micrograms (ug), or any other unit of weight; the molar (concentration) ratios may be expressed in unit selected from moles (M), millimoles (mM), micromoles (μM), and other molar units.

In a preferred embodiment, in the composition described herein, the GSK3β inhibitor (or GSK3β inhibitor CHIR99021), the TGFβ inhibitor (or TGFβ inhibitor SB431542 or/and A83-01) are present at a ratio of part by weight of: (0.046-4.65):(0.038-7.68); preferably, (0.232-2.325):(0.192-3.84); or at a molar ratio of: (0.1-10):(0.1-20); preferably, (0.5-5):(0.5-10).

In another preferred embodiment, in the composition described herein, the GSK3β inhibitor (or GSK3β inhibitor CHIR99021), the TGFβ inhibitor (or TGFβ inhibitor SB431542 or/and A83-01), and the retinoid compound (or retinoic acids) are present at a ratio of part by weight of: (0.046-4.65):(0.038-7.68):(0.03-6.0); preferably, (0.232-2.325):(0.192-3.84):(0.15-3); or at a molar ratio of: (0.1-10):(0.1-20):(0.1-20); preferably, (0.5-5):(0.5-10):(0.5-10).

In another preferred embodiment, in the composition described herein, the GSK3β inhibitor (such as GSK3β inhibitor CHIR99021), the TGFβ inhibitor (such as TGFβ inhibitor SB431542 or/and A83-01), the retinoid compound (such as retinoic acids), the BMP inhibitor (such as BMP inhibitor LDN-193189) and BrdU are present at a ratio of part by weight of: (0.046-4.65):(0.038-7.68):(0.03-6.0):(0.02-4.65):(0.15-30); preferably, (0.232-2.325):(0.192-3.84):(0.15-3):(0.203-2.03):(1.5-15); or in the solution state, at a molar ratio of: (0.1-10):(0.1-20):(0.1-20):(0.05-10):(0.5-100); preferably, (0.5-5):(0.5-10):(0.5-10):(0.5-5):(5-50).

In another preferred embodiment, in the composition described herein, the GSK3β inhibitor (such as GSK3β inhibitor CHIR99021), the TGFβ inhibitor (such as TGFβ inhibitor SB431542 or/and A83-01), the retinoid compound (such as retinoic acids), the BMP inhibitor (such as BMP inhibitor LDN-193189) and EdU are present at a ratio of part by weight of: (0.046-4.65):(0.038-7.68):(0.03-6.0):(0.02-4.65):(0.125-25); preferably, (0.232-2.325):(0.192-3.84):(0.15-3):(0.203-2.03):(1.25-12.5); or in the solution state, at a molar ratio of: (0.1-10):(0.1-20):(0.1-20):(0.05-10):(0.5-100); preferably, (0.5-5):(0.5-10):(0.5-10):(0.5-5):(5-50).

In certain preferred embodiments, the composition comprises the components at the amounts (based on parts by weight or mola ratio in solution) as set forth in Table 2 or Table 3.

TABLE 2

| Component | Parts by weight (ratio) | Preferred parts by weight (ratio) |
|---|---|---|
| GSK3β inhibitor | 0.046-4.65, for example, 0.1, 0.5, 1, 2, 3, 4 | 0.232-2.325 |
| TGFβ inhibitor | 0.038-7.68, for example, 0.1, 0.5, 1, 2, 3, 5, 7 | 0.192-3.84 |
| Optionally and preferably, retinoid compound | 0.03-6.0, for example, 0.1, 0.5, 1, 2, 3, 4, 5 | 0.15-3 |
| Optionally and preferably, BMP inhibitor | 0.02-4.65, for example, 0.05, 0.1, 0.5, 1, 2, 3, 4 | 0.203-2.03 |
| Optionally and preferably, BrdU or/and EdU | BrdU: 0.15-30, for example, 1, 3, 5, 10, 15, 20, 25 EdU: 0.125-25, for example, 0.5, 1, 3, 5, 10, 15, 20 | BrdU: 1.5-15 EdU: 1.25-12.5 |

TABLE 3

| Component | Molar ratio | Preferred molar ratio |
|---|---|---|
| GSK3β inhibitor | 0.1-10, for example, 0.5, 1, 3, 5, 7, 9 | 0.5-5 |
| TGFβ inhibitor | 0.1-20, for example, 0.5, 1, 3, 5, 7, 9, 12, 15, 18 | 0.5-10 |
| Optionally and preferably, retinoid compound | 0.1-20, for example, 0.5, 1, 3, 5, 7, 9, 12, 15, 18 | 0.5-10 |
| Optionally and preferably, BMP inhibitor | 0.05-10, for example, 0.1, 0.5, 1, 3, 5, 7, 9 | 0.5-5 |
| Optionally and preferably, BrdU or/and EdU | 0.5-100, for example, 3, 5, 10, 20, 40, 60, 80 | 5-50 |

The ranges listed in Tables 1 and 2 are for reference. It should be understood that when used to develop a pharmaceutical composition, the effective dosage of the composition used may vary with the manner of administration, the type of tumour being treated and the severity of the disease. And, when used in vivo, "weight/kg (body weight)" is usually used as a dosage unit; when the small molecule composition is applied to large animals and patients having tumor, the effective dose of the large animal or human is converted by the corresponding professional conversion formula according to the use dose of the small animal (including solid-state or solution-state dose conversion). It also belongs to the protection scope of the present invention.

As used herein, the "GSK3β inhibitor" is a generic term for inhibitors that inhibit the GSK3β signaling pathway in cells, including but not limited to GSK3β signaling pathway inhibitors of the same class that have the same function or targeting the same induction site(s), as represented by CHIR-99021, BIO, IM-12, TWS119, etc.

CHIR-99021 (CT99021), an inhibitor having IC50 of 10 nM and 6.7 nM on GSK-3α and β respectively, 500-fold stronger than its inhibition on CDC2, ERK2 and other kinases;

CHIR-99021 (CT99021) HCl, hydrochloride of CHIR-99021, is a GSK-3α/β inhibitor, having an IC50 of 10 nM/6.7 nM in acellular test; useful in distinguishing GSK-3 and its closest homologues Cdc2 and ERK2;

BIO, a specific GSK-3 inhibitor, having an IC50 of 5 nM on GSK-3α/β in acellular test;

IM-12, a selective GSK-3β inhibitor, having an IC50 of 53 nM, enhancing Wnt signaling pathway;

TWS119, a GSK-3β inhibitor, having an IC50 of 30 nM in acellular test;

1-Azakenpaullone, a highly selective GSK-3β inhibitor, having an IC50 of 18 nM;

CHIR-98014, a GSK-3α/β inhibitor, having an IC50 of 0.65 nM/0.58 nM in acellular test;

Tideglusib, an irreversible, non-ATP competitive GSK-3β inhibitor, having an IC50 of 60 nM in acellular test;

AR-A014418, an ATP competitive and selective GSK3β inhibitor, having an IC50 and of 104 nM and a Ki of 38 nM in acellular test;

LY2090314, a GSK-3 inhibitor, having an IC50 of 1.5 nM/0.9 nM on GSK-3α/β;

SB216763, a selective GSK-3α/β inhibitor, having an IC50 of 34.3 nM;

AZD1080, biologically effective, selective, brain permeable GSK3 inhibitor for oral-administration, inhibiting human GSK3α and GSK3β with Ki of 6.9 nM and 31 nM respectively, having a selectivity of 14-fold higher than on CDK2, CDK5, CDK1 and Erk2.

As a preferred embodiment of the present invention, the GSK3β inhibitor is CHIR-99021, also referred to as CT99021, having a structure as set forth in Formula (I) below.

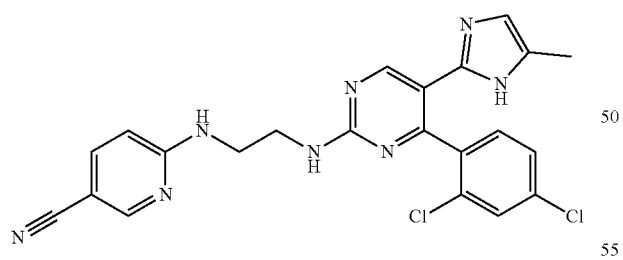

(I)

As used herein, the "TGFβ inhibitor" is a generic term for inhibitors that inhibit the TGFβ signaling pathway in cells, including but not limited to TGFβ signaling pathway inhibitors of the same class that have the same function or target the same induction site(s), as represented by SB431542, A83-01, SB525334, LY2109761, RepSox, etc.

SB-431542, a selective ALK5 inhibitor, having an IC50 of 94 nM, 100-fold stronger than inhibition on p38, MAPK and other kinases;

A83-01, an inhibitor having IC50 of 12, 45 and 7.5 nM on ALK5, ALK4 and ALK7 respectively;

SB525334, a selective TGFβ receptor I (ALK5) inhibitor, having an IC50 of 14.3 nM in acellular test, having an effect on ALK4 4-fold lower than on ALK5, no activity to ALK2, 3 and 6;

LY2109761, a novel selective dual inhibitor on TGF-β receptor type I/II (TβRI/II) with Ki respectively being 38 nM and 300 nM in acellular test;

RepSox, a selective TGFβR-1/ALK5 inhibitor, acting on the binding between ATP and ALK5 and the autophosphorylation of ALK5 with IC50 respectively being 23 nM and 4 nM in acellular test.

SD-208, a selective TGF-βRI (ALK5) inhibitor having an IC50 of 48 nM, and having a selectivity more than 100-fold higher than on TGF-βRII;

GW788388, a selective ALK5 inhibitor, having an IC50 of 18 nM in acellular test, also inhibiting TGF-β type II receptor and activin type II receptor, but not BMP type II receptor;

SB505124, a selective TGFβR inhibitor, acting on ALK4 and ALK5 with IC50 being 129 nM and 47 nM respectively in acellular test, also inhibiting ALK7, but not ALK1, 2, 3 or 6;

EW-7197, a selective biologically inhibitor of TGF-β receptor for oral-administration, with IC50 being 13 nM and 11 nM on ALK4/ALK5 respectively.

As a preferred embodiment of the present invention, the TGFβ inhibitor is SB 431542 (or referred to as SB-431542), having a structure set forth in Formula (II) below.

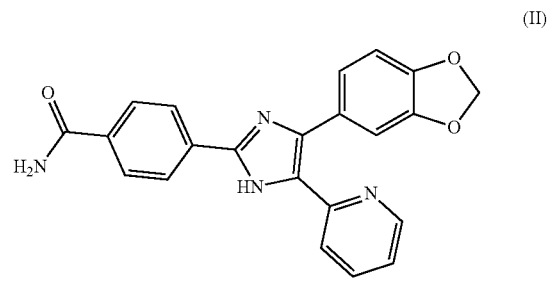 [SMILES: NC(=O)c1ccc(-c2nc(-c3ccc4c(c3)OCO4)c(-c3ccccn3)[nH]2)cc1]

(II)

As a preferred embodiment of the present invention, the TGFβ inhibitor is A83-01 (or referred to as A8301), having a structure set forth in Formula (III) below.

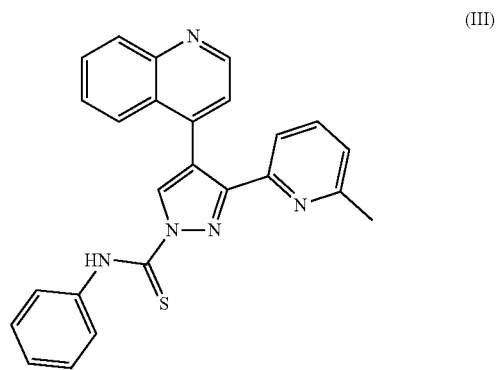 [SMILES: Cc1cccc(-c2nn(C(=S)Nc3ccccc3)cc2-c2ccnc3ccccc23)n1]

(III)

As used herein, the retinoids include but are not limited to retinoid differentiation inducing agents or compounds of the same class that have the same function or target the same induction site(s), or combinations thereof, represented by retinoic acids (RAs), also known as all trans retinoic acid (ATRA), 13-cis retinoic acid (13-CRA), 9-cis-retinoic acid (9-CRA).

Retinoids have the function of regulating proliferation, differentiation and physiological apoptosis of cells because they can activate the corresponding retinoic acid receptor (RAR) and retinoid x receptor (RXR) proteins, and regulate the transcription activity of specific nuclear genes via specific binding with retinoic acid response elements (RARE) to produce biological effects. Many of retinoids and isomer derivatives thereof have the same or similar functions and can therefore be useful as differentiation inducing agents or compounds.

Retinoids are a group of oxidative metabolites or derivatives of vitamin A (retinol) and synthetics with similar structures to vitamin A, including natural and synthetic types, such as, retinoic acid (RA) (also referred to as tretinoin, all trans retinoic acids), 13-cis retinoic acid (13-CRA), etretinate, 9-cis retinoic acid (9-CRA), UAB7, UAB8, isotretinoin, Viaminate (Fenretinide), Acitretin, Etretinate, Tazarotene, Adapalene, TTNPB, 3-methyl-TTN PB, AM80, AM580, CD437, Targretin, LGD1069 and other retinoids having the same function, in which RA or ATRA, TTNPB, AM80 and AM580 are RAR-specific agonists. LGD 1069 and SR 11237 are RXR-specific agonists; 9-CRA and 3-methyl-TTNPB are agonists of both of the receptor proteins, as pan-agonists.

As a preferred embodiment of the present invention, the retinoic acid (RA), also referred to as all trans retinoic acid (ATRA), tretinoin, vitamin A acid, vitamin formate, retinoic acid, all-trans-tretinoin, vitamin A acid, has a structure set forth in Formula (IV) below.

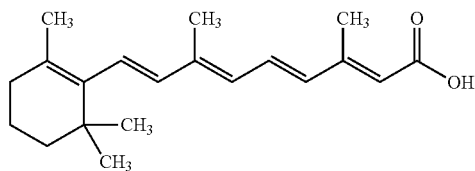

(IV)

As used herein, the "BMP inhibitor" is a generic term for inhibitors that inhibit the BMP signaling pathway in cells, including but not limited to: BMP signaling pathway inhibitors of the same class that have the same function or target the same induction site(s), represented by LDN-193189, LDN193189 HCl, K02288, DMH1 etc.

LDN-193189, a selective BMP signaling pathway inhibitor, inhibiting transcription activity of BMP type I receptor ALK2 and ALK3 with IC50 of 5 nM and 30 nM respectively in C2C12 cells, having a selectivity on BMP 200-fold higher than on TGF-β. Cas: 1062368-24-4.

LDN193189 HCl, a hydrochloride of LDN193189, is a selective BMP signaling inhibitor. It can inhibit transcription activity of BMP type I receptors ALK2 and ALK3, with IC50 of 5 nM and 30 nM respectively in C2C12 cells, and having a selectivity on BMP 200-fold higher than on TGF-β.

K02288, a highly selective inhibitor of type I BMP receptor, having an IC50 of 1.1, 1.8, 6.4 nm on ALK2, ALK1 and ALK6 respectively, showing slight inhibiting activity on other ALK5 (3, 4, 5) and ActRIIa.

DMH1, a selective inhibitor of BMP receptor, inhibiting ALK2, having an IC50 of 107.9 nM, with no inhibiting activity on AMPK, ALK5, KDR (VEGFR-2) and PDGFR.

As a preferred embodiment of the present invention, the BMP inhibitor is LDN-193189 (or referred to as LD-N193189), having a structure as set forth in Formula (V) below.

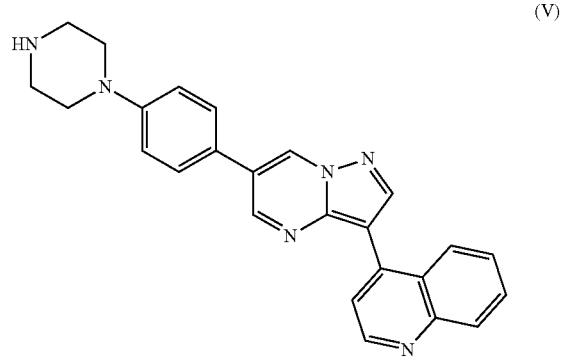 [SMILES: c1ccc2c(-c3cnn4cc(-c5ccc(N6CCNCC6)cc5)cnc34)ccnc2c1]

(V)

As used herein, BrdU's full name is "5-bromodeoxyuridine", also known as: 5-bromo-2'-deoxyuridine; 5-bromo-2-deoxyuridine; 5-bromo-1-(2-deoxy-β-D-ribofuranose) uracil; 5-bromodeoxyuridine; bromodeoxyuridine; 5-Bromo-2"-Deoxyuridine; abbreviation: BrdU or 5-BrdU. Other names include: 5-Bromo-2-deoxyUridine; Br-dU; BUdR; 5-Bromodeoxyuridine; Brdu. It is a derivative of thymine, and also a nucleoside analog of thymine, which can be an alternative to thymine in the phase of DNA synthesis (S phase), which can be injected in vivo or introduced in cell cultures, followed by adding Brdu monoclonal antibody and ICC staining with, to detect proliferative cells. It has been generally used as a cell marker, but was recently reported with some newly found activities.

As a preferred embodiment of the present invention, BrdU has a structure as set forth in Formula (VI) below.

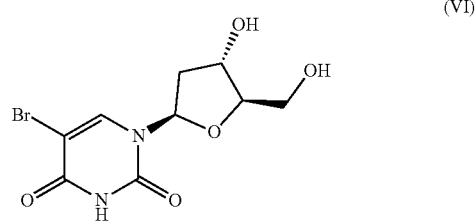 [SMILES: O=c1[nH]c(=O)n([C@H]2C[C@H](O)[C@@H](CO)O2)cc1Br]

(VI)

As used herein, EdU is named "5-ethynyl-2'-deoxyuridine"; also known as: 5-ethynyl-2-deoxyuridine; 5-ethynyl-2'-deoxyuridine; ethynyl-deoxyuridine; 5-Ethynyl-2'-deoxyuridine, abbreviation: EdU; also known as EYdU; Uridine; 5-Ethynyl-durd; 5-Ethynyl-2'-dU; 2' deoxyuridine; 5-ethynyl; 2'-deoxy-5-ethynyluridine; 2'-deoxy-5-ethynyluridin. EdU is a new type of thymidine analogue, which can be introduced into dividing cells. It shows cytotoxicity at higher doses. EdU can be detected using a fluorescent azide which can form a covalent bond with EdU. Unlike the commonly used bromodeoxyuridine, EdU can be detected without thermal or acidic treatment. It is usually used as a cell marker, but was recently reported with some newly found activities.

As a preferred embodiment of the present invention, EdU has a structure as set forth in Formula (VII) below.

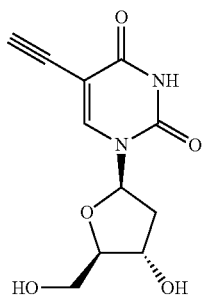

(VII)

The present invention also includes compounds, pharmaceutical preparations, analogues and/or salts, hydrates or precursors thereof that are equivalent to the above described compounds I, II or III, IV, V, VI or VII; as well as the compounds naturally occurring and artificially synthesized.

Analogues of the compounds include, but are not limited to: isomers, racemates of the compounds. The compounds have one or more asymmetric centers. Therefore, these compounds may exist as racemic mixtures, individual enantiomers, individual diastereomers, diastereomeric mixtures, cis- or trans-isomers.

The "salts" include, but are not limited to: (1) salts formed with inorganic acids such as hydrochloric acid, sulfuric acid, nitric acid, phosphoric acid, etc.; (2) salts formed with organic acids such as acetic acid, oxalic acid, butanedioic acid, tartaric acid, methanesulfonic acid, maleic acid, or arginine. Other salts include salts formed with alkali or alkaline earth metals such as sodium, potassium, calcium or magnesium.

The "precursor of a compound" refers to a compound that can be converted into any of the above described compounds in a culture medium, upon application or treatment of an appropriate method, or a salt or solution composed of any of the above described compounds.

In the composition described herein, the GSK3β inhibitor (or GSK3β inhibitor CHIR99021) and the TGFβ inhibitor (or TGFβ inhibitor SB431542 or/and A83-01) are present at a weight ratio of: (0.046-4.65):(0.038-7.68); preferably, (0.232-2.325):(0.192-3.84); or, at a molar ratio of (0.1-10):(0.1-20) when in a solution state; preferably (0.5-5):(0.5-10). This small molecule composition is useful for chemically inducing the transdifferentiation of tumor cells directly into non-oncogenic cells and accompanying apoptosis of tumor cells. This composition tends more to induce apoptosis of tumor cells, less to transdifferentiate the tumor cells.

As a preferred embodiment of the present invention, the composition further comprises: a retinoid compound, 0.03-6.0 parts by weight; preferably 0.15-3.0 parts by weight; or at a final molar concentration of 0.1-20 μM in a solution state; preferably 0.5-10 μM. Addition of this component can facilitate and enhance the transformation or apoptosis of tumor cells, and expand the applicable types and range of tumors.

In the composition with the addition of the above component, the GSK3β inhibitor (or GSK3β inhibitor CHIR99021), the TGFβ inhibitor (or TGFβ inhibitor SB431542 or/and A83-01) and the retinoid compound (or retinoic acids) are present at a weight ratio of (0.046-4.65):(0.038-7.68):(0.03-6.0); preferably, (0.232-2.325):(0.192-3.84):(0.15-3); or at a molar ratio of (0.1-10):(0.1-20):(0.1-20) when in a solution state; preferably, (0.5-5):(0.5-10):(0.5-10).

Into the composition described herein, one or more components can be added, which is(are) selected from: BMP inhibitor LDN-193189:0.02-4.65 parts by weight; preferably 0.203-2.03 parts by weight; or at a final concentration of 0.05-10 μM in a solution state; preferably 0.5-5 μM; or/and BrdU, or/and EdU: 0.15-30 parts by weight (BrdU), 0.125-25 parts by weight (EdU); preferably 1.5-15 parts by weight (BrdU), 1.25-12.5 (EdU); or at a final concentration of 0.5-100 μM (BrdU or EdU) in a solution state; preferably 5-50 μM (BrdU or EdU). Addition of the component(s) can further facilitate or enhance the transdifferentiation or apoptosis of some certain tumor cells of high malignancy.

In another preferred embodiment, in the composition described herein, the GSK3β inhibitor (such as GSK3β inhibitor CHIR99021), TGFβ inhibitor (such as TGFβ inhibitor SB431542 or/and A83-01), retinoids (such as retinoic acids), BMP inhibitor (such as BMP inhibitor LDN-193189) and BrdU are present at a weight ratio of: (0.046-4.65):(0.038-7.68):(0.03-6.0):(0.02-4.65):0.15-30; preferably, (0.232-2.325):(0.192-3.84):(0.15-3):(0.203-2.03):(1.5-15); or at a molar weight of (0.1-10):(0.1-20):(0.1-20):(0.05-10):(0.5-100) when in a solution state; preferably, (0.5-5):(0.5-10):(0.5-10):(0.5-5):(5-50).

In another preferred embodiment, in the composition described herein, the GSK3β inhibitor (such as GSK3β inhibitor CHIR99021), TGFβ inhibitor (such as TGFβ inhibitor SB431542 or/and A83-01), retinoids (such as retinoic acids), BMP inhibitor (such as BMP inhibitor LDN-193189) and EdU are present at a weight ratio of (0.046-4.65):(0.038-7.68):(0.03-6.0):(0.02-4.65):(0.125-25); preferably, (0.232-2.325):(0.192-3.84):(0.15-3):(0.203-2.03):(1.25-12.5); or, at a molar ratio of (0.1-10):(0.1-20):(0.1-20):(0.05-10):(0.5-100) when in a solution state; preferably, (0.5-5):(0.5-10):(0.5-10):(0.5-5):(5-50).

The dosage form of the composition described herein is not particularly limited, and can be any dosage form suitable for use in mammals; the dosage forms that can be prepared include powders, pulvis, tablets, pills, capsules, sustained release agents, controlled-release agents and other solid dosage forms; injections, infusions, suspensions, and other liquid dosage forms; and gaseous formulations, semi-solid dosage forms, and the like. Preferably, the dosage form can be, but is not limited to, solid dosage forms such as powders, granules, capsules, sustained release agents, tablets and the like, liquid dosage forms such as injections, infusions, solutions, suspensions, and the like.

The composition of the present invention can be prepared using different methods according to the selected dosage form and the administration route. Those skilled in the art can prepare the composition of the present invention by using the preparation process of conventional pharmaceutical compositions according to the combinations and ratios provided herein.

It will be understood that although in the specific embodiments several composition forms have been exemplified, one skilled in the art can also derive therefrom that any other combination of the present invention can also produce a prominent effect.

The inventors demonstrated for the first time that the small molecule composition described herein can be used in preparing drugs or pharmaceutical formulations for preventing, ameliorating, or treating tumors. When used to prevent, ameliorate, or treat tumors, the effective amount of the composition used may vary with the mode of administration and the type of tumor being treated and the severity of the disease. The specific situation is determined according to the subject's individual condition, which is within the range judged by a skilled physician or pharmacist.

In the present invention, the tumor or tumor cells include but are not limited to liver cancer, nasopharyngeal cancer, lung cancer, gastric cancer, colorectal cancer, pancreatic cancer, breast cancer, ovarian cancer, prostate cancer, osteosarcoma, lymphoma, leukemia, esophageal cancer, cervical cancer, oral cancer, salivary gland tumor, nasal and paranasal sinus cancer, laryngeal cancer, otic tumor, ocular tumor, thyroid tumor, mediastinal tumor, chest wall, pleural tumor, small intestine tumor, biliary tract tumor, pancreas and periampullary neoplasms, mesenteric and retroperitoneal neoplasms, renal neoplasms, adrenal neoplasms, bladder neoplasms, testicular neoplasms, penile neoplasms, endometrial carcinomas, ovarian malignancies, malignant trophoblastic neoplasms, vulvar and vaginal carcinomas, malignant lymphomas, multiple myeloma, soft tissue tumors, bone tumors, skin and adnexal tumors, malignant melanoma or nervous system tumors, and other hematological and solid tumors or their cells. Hepatic carcinoma or hepatoma carcinoma cells are preferred.

Culture Media and Agents

The invention further provides a culture medium for use in inducing reprogramming (transdifferentiation) of human tumor cells directly into non-oncogenic cells and accompanying apoptosis of tumor cells by using the small molecule composition, which is also referred to herein as a culture medium for tumor cell transdifferentiation with accompanying apoptosis.

According to the formulation of the composition provided herein, compositions of small molecules at specific final concentrations are prepared. As a preferred embodiment, depending on their solute characters and solubilities, specific components of the small molecule composition are each dissolved in DMSO (dimethyl sulfoxide) or an other organic solvent or aqueous solvent as appropriate to produce a concentrated solution (ranged 1:50-1:10,000); then the concentrated solution of each small molecule is diluted according to its required final concentration in the composition; the so-obtained composition is added into a basal cell culture medium containing 10% calf serum, 1% penicillin-streptomycin mix (100×) (or a serum-free medium containing various cytokines or growth factors), to produce the culture medium for tumor cell transdifferentiation and accompanying apoptosis as described, in which the percentage content for each component in the medium can vary within a range of ±50%; preferably ±30%; more preferably ±20%, for example ±10%, ±5% of the specified value (percentages refer to "% (v/v)").

As a preferred embodiment of the present invention, the basal cell culture medium includes but is not limited to: DMEM/F12, MEM, DMEM, F12, IMDM, RPMI1640, Neuronal basal or Fischers etc., all of which are commercially available.

As a preferred embodiment of the present invention, the "serum-free cell culture medium" refers to a serum-free cell culture medium containing various nutrients (such as growth factors, tissue extracts, etc.) that support cell proliferation and biological responses. That is, a cell culture medium obtained by incorporating additives such as cytokines or growth factors other than serum.

As a preferred embodiment of the present invention, the serum-free medium containing various cytokines or growth factors includes but is not limited to ITS, N2, B27, etc., all of which can be prepared in the laboratory or commercially available.

It will be understood that those skilled in the art are familiar with the preparation or purchase of the basal cell culture medium or the serum-free medium. The basal cell culture medium or the serum-free medium is therefore not limited to those exemplified in the invention.

As a preferred embodiment, the preparation of the "culture medium for tumor cell transdifferentiation accompanied by apoptosis" can be conducted as follows:

(1) Mix (a) a GSK3β inhibitor (or GSK3β inhibitor CHIR-99021), 0.046-4.65 parts by weight; preferably 0.232-2.325 parts by weight; or at a final concentration of 0.1-10 μM in a solution state; preferably 0.5-5 μM; and (b) a TGFβ inhibitor (or TGFβ inhibitor SB431542 or/and A83-01), 0.038-7.68 parts by weight; preferably 0.192-3.84 parts by weight; or at a final concentration of 0.1-20 μM in a solution state; preferably 0.5-10 μM, to obtain the small molecule composition described herein for chemically inducing the reprogramming of human tumor cells directly into non-oncogenic cells and accompanying apoptosis in tumor cells.

(2) Based on the composition of (1), further additives can be added, including: retinoids (or retinoic acids), 0.03-6.0 parts by weight; preferably 0.15-3 parts by weight; or at a final concentration of 0.1-20 μM in a solution state; preferably 0.5-10 μM the addition of which can facilitate and enhance the transdifferentiation and the accompanied apoptosis of tumor cells, and expand the applicable range or types of tumors.

(3) Based on the composition of (2), one or two components selected from the following group can be added: BMP inhibitor LDN-193189:0.02-4.65 parts by weight; preferably 0.203-2.03 parts by weight; or at a final concentration of 0.05-10 μM in a solution state; preferably 0.5-5 μM; or/and BrdU, or/and EdU: 0.15-30 parts by weight (BrdU), 0.125-25 (EdU); preferably 1.5-15 parts by weight (BrdU), 1.25-12.5 (EdU); or (BrdU or/and EdU) at a final concentration of 0.5-100 μM in a solution state; preferably 5-50 μM; the addition of which can further facilitate or enhance the transformation or apoptosis of some certain tumor cells.

(4) Mix the above small molecule compositions to obtain the "culture medium for tumor cell transdifferentiation accompanied by apoptosis".

Further provided herein are agents for injection or oral administration to experimental animals for chemically inducing reprogramming (transdifferentiation) of human tumor cells directly into non-oncogenic cells and accompanying apoptosis of the tumor cells.

As a preferred embodiment of the present invention, for any one of the foregoing small molecule compositions, the corresponding dosage by kilogram body weight is calculated. Then it is dissolved in a solution of Captisol (1-30%) or Tween-80 (5%) to obtain the agents for injection or oral administration to experimental animals; or a concentrated solution containing each of the components in the composition at a respective amount is added into an injectable normal saline or a phosphate solution (with or without 5% FBS) to obtain the agents for injection or oral administration to experimental animals, preferably dissolved in Captisol (1-30%).

Culture Method

Also disclosed herein is a method of inducing reprogramming (transdifferentiation) of human tumor cells directly into non-oncogenic cells and accompanying apoptosis of the tumor cells, including:

(1) Preparation of concentrated solution: dissolving each of the components of the composition of any of claims 1-6 in an organic solvent or an aqueous solvent to obtain a concentrated solution; preferably, the organic solvent includes dimethylsulfoxide; and preferably, the aqueous solvent includes water, normal saline, phosphate buffer;

(2) Formulation of medium: diluting the concentrated solution of step (1) in a basal cell culture medium containing 5-20% calf serum and 1% penicillin-streptomycin mix (100×) or a serum-free medium containing various cytokines or growth factors, (so that each of the components has a concentration as defined for the composition of any of claims 1-6), to produce a medium for inducing the transdifferentiation and the accompanying apoptosis of tumor cells;

in which the percentage content for each component in the medium can vary within a range of ±50%; preferably ±30%; more preferably ±20%, for example ±10%, ±5% of the specified value.

(3) Induction of transdifferentiation accompanied by apoptosis of tumor cells: suspending the tumor cells in the medium formulated in step (2) for inducing the transdifferentiation with accompanying apoptosis of tumor cells, and plating the suspension to prepare the treatment group;

adding the same solvent as used in the treatment group (such as DMSO or other solvents) into the basal cell culture medium containing 10% calf serum, 1% penicillin-streptomycin mix (100×) (or the serum-free medium containing various cytokines or growth factors) the same as used in the treatment group, to prepare the "control medium" (percentages refer to "% (v/v)"); then adding and suspending the same number of tumor cells as in the treatment group into the "control medium", plating the suspension to prepare the control group;

culturing the cells at 37° C., with medium changed every 2-4 days and cells subcultured every 3-7 days;

(4) Continuous passage culture inducing the transdifferentiation and the accompanied apoptosis of tumor cells: discarding the original culture medium, washing the cells once with PBS, adding a digestion solution for cell digestion at 37° C. for 1-5 minutes; stopping the cell digestion, centrifuging the cells and discarding the supernatant, recompensing cell pellets and plating at a ratio of 1:1-1:3; culturing the cells according to steps (1) and (2), with the medium changed every 2-4 days and cells subcultured every 3-7 days; the digestive solution used comprises trypsin, EDTA, Acutase, TrypleE, etc.;

(5) Induction of the transdifferentiation accompanied by apoptosis in tumor cells to obtain normal or non-oncogenic cells: continuous culturing the tumor cells according to steps (3) and (4) for transdifferentiaton and apoptosis for 1-3 weeks, washing off the apoptotic cells with PBS to obtain the transdifferentiated non-oncogenic cells; the so-obtained cells can be used in further researches; detection of cellular apoptosis: culturing for the transdifferentiation accompanied by apoptosis in the tumor cells are conducted as described above, and the tumor cells cultured for different durations are stained using Annexin V-FITC detection kit (Biovision) and detected via flow cytometry; detailed procedures can be found in the instruction of the kit.

Activity assays of the transdifferentiated oncogenic cells: the transdifferentiation accompanied by apoptosis of the tumor cells are conducted as above, and non-oncogenic cells cultured for different durations are obtained and tested on activity.

The small molecule compositions for transdifferentiation accompanied by apoptosis of tumor cells described herein as well as the culture media and agents prepared from same and the experimental processes using same can be utilized not only in the preparation of anti-tumor drugs, but also in the research and study on the method and mechanism of preventing and treating tumors, preclinical studies, pharmacological and toxicological safety testing. The so-obtained non-oncogenic cells can be used in function detection, tumorigenic multiple target assay, preclinical studies and the like. The method described herein not only opens up a new field for the prevention and treatment of tumors, but also has broad application prospects. It enriches the theory of stem cell reprogramming, expands its application, and is of great scientific significance and great application value.

The Beneficial Effects of the Present Invention are:

1. We're the first to presented here a novel idea based on cell reprogramming mechanism: tumor cells can be transdifferentiated directly into targeting cells by using combined inducing factors, wherein the factors are selected for their ability to construct and maintain the specific gene expression profile or biological behavior of the cells of interests and to overcome various "barriers" in the process of reprogramming of the starting cells.

2. We're the first to apply cell reprogramming mechanism and chemically-induced direct reprogramming (transdifferentiation) process in tumor therapy researches, which produced expected effects. By using small molecules, the hepatoma cells were induced and transdifferentiated into non-oncogenic functional hepatocytes (in vitro), which is accompanied by apoptosis of the tumor cells. The mechanism and process are feasible to induce transdifferentiation in other tumor cells to give consistent results.

3. We're the first to apply the chemical-induced transdifferentiation on hepatoma cells in vivo (hepatoma tissue PDX animal model). The results show massive necrosis of hepatic carcinoma tissue in vivo, indicating loss of structure integrity of hepatic carcinoma, and high expression of HNF4a indicative of the transdifferentiated state. It has been demonstrated that the small molecule composition is potentially therapeutic effect on hepatic carcinoma.

4. In the present invention, the small molecules are stable in property, providing controllable acting time, dosage and combination mode, and stable and reliable effect.

5. There's no need to introduce exogenous genes or change the genome structure of the cells, thus providing improved safety and reliability by avoiding new carcinogenic risks caused by introduction of exogenous genes or any change in genes.

6. We're the first to use multi-target induction of transdifferentiation of tumor cells into normal (non-oncogenic) cells without using cytocidal agents to assist control or treatment of tumor, thus avoiding damage to normal cells (such as normal human fibroblast and hepatocytes) and having no toxic and side effect.

7. We achieved for the first time the small molecule combination-induced transdifferentiation of tumor cells directly into non-oncogenic cells, without reprogramming into iPSCs, thus avoiding carcinogenic risks caused by stem cells.

8. Further results show that in addition to hepatoma cells, cells from other tumors, such as nasopharyngeal cancer, lung cancer, gastric cancer, colorectal cancer, pancreatic cancer, breast cancer, ovarian cancer, prostate cancer, osteosarcoma, lymphoma, leukemia, and other hematologic tumors and solid tumors, also respond to the induction using small molecule composition and exhibit consistent or comparable effects of induced transdifferentiation accompanied by apoptosis.

9. The small molecule composition is promising as a new method, a new means or a new drug for controlling or treating hepatic carcinoma and other malignant tumors with high efficiency and low toxicity. It can also be prepared into media and reagents for R&D of chemical induction of reprogramming directly into non-oncogenic cells in tumor cells.

10. The small molecule composition and the method described herein for inducing tumor cell transdifferentiation accompanied by apoptosis are highly efficient in operability, cost, production and application.

11. The invention enriches the reprogramming theory and broadens its application scope; it opens up a new field of tumor treatment research; and provides new ideas, new methods and new drugs for clinical tumor treatment.

The present invention is further described in combination in particular with the examples below. It will be understood that these examples are only for illustrating the present invention and are not intended to limit the scope of the present invention. The experimental processes that do not specify the specific conditions in the following examples are generally performed according to conventional conditions such as those described in J. Sambrook et al., Molecular Cloning: A Laboratory Manual, 3$^{rd}$ Edition, Science Press, 2002, or according to the conditions recommended by the manufacturers.

Example 1. Formulations of Small Molecule Compositions, Culture Media and Agents for Tumor Cell Transdifferentiation Accompanied by Apoptosis The compositions and culture media were formulated as follows, according to the molar concentrations or weight concentrations:

1. Formulations of Small Molecule Compositions Designed for Tumor Cell Transdifferentiation Accompanied by Apoptosis Compositions were designed according to the following formulations:

(1) Composition 1 for Tumor Cell Transdifferentiation Accompanied by Apoptosis
 GSK3β inhibitor CHIR-99021: at a final concentration of 2 μM;
 TGFβ inhibitor SB431542: at a final concentration of 5 μM.

(2) Composition 2 for Tumor Cell Transdifferentiation Accompanied by Apoptosis
 GSK3β inhibitor CHIR-99021: at a final concentration of 3 μM;
 TGFβ inhibitor SB431542: at a final concentration of 2 μM.

(3) Composition 3 for Tumor Cell Transdifferentiation Accompanied by Apoptosis
 GSK3β inhibitor CHIR-99021: at a final concentration of 5 μM;
 TGFβ inhibitor A83-01: at a final concentration of 2 μM.

(4) Composition 4 for Tumor Cell Transdifferentiation Accompanied by Apoptosis
 GSK3β inhibitor CHIR-99021: at a final concentration of 4 μM;
 TGFβ inhibitor A83-01: at a final concentration of 3 μM;
 Retinoic acid (RA): at a final concentration of 0.5 μM.

(5) Composition 5 for Tumor Cell Transdifferentiation Accompanied by Apoptosis
 GSK3β inhibitor CHIR-99021: at a final concentration of 3 μM;
 TGFβ inhibitor SB431542: at a final concentration of 5 μM;
 Retinoic acid (RA): at a final concentration of 3 μM.

(6) Composition 6 for Tumor Cell Transdifferentiation Accompanied by Apoptosis
 GSK3β inhibitor CHIR-99021: 2 μM;
 TGFβ inhibitor SB431542: at a final concentration of 2 μM;
 Retinoic acid (RA): at a final concentration of 5 μM.

(7) Composition 7 for Tumor Cell Transdifferentiation Accompanied by Apoptosis
 GSK3β inhibitor CHIR-99021: at a final concentration of 3 μM;
 TGFβ inhibitor SB431542: at a final concentration of 1 μM;
 Retinoic acid (RA): at a final concentration of 0.5 μM;
 BMP inhibitor LDN-193189: at a final concentration of 0.5 μM.

(8) Composition 8 for Tumor Cell Transdifferentiation Accompanied by Apoptosis
 GSK3β inhibitor CHIR-99021: at a final concentration of 3 μM;
 TGFβ inhibitor SB431542: at a final concentration of 5 μM;
 Retinoic acid (RA): at a final concentration of 3 μM;
 BMP inhibitor LDN-193189: 0.5 μM.

(9) Composition 9 for Tumor Cell Transdifferentiation Accompanied by Apoptosis
 GSK3β inhibitor CHIR-99021: at a final concentration of 3 μM;
 TGFβ inhibitor SB431542: at a final concentration of 2 μM;
 Retinoic acid (RA): at a final concentration of 10 μM;
 BMP inhibitor LDN-193189: at a final concentration of 0.5 μM.

(10) Composition 10 for Tumor Cell Transdifferentiation Accompanied by Apoptosis
 GSK3β inhibitor CHIR-99021: at a final concentration of 3 μM;
 TGFβ inhibitor SB431542: at a final concentration of 5 μM;
 BMP inhibitor LDN-193189: 2 μM.

(11) Composition 11 for Tumor Cell Transdifferentiation Accompanied by Apoptosis
 GSK3β inhibitor CHIR-99021: at a final concentration of 3 μM;
 TGFβ inhibitor SB431542: at a final concentration of 7.5 μM;
 BMP inhibitor LDN-193189: at a final concentration of 0.5 μM.

(12) Composition 12 for Tumor Cell Transdifferentiation Accompanied by Apoptosis
 GSK3β inhibitor CHIR-99021: at a final concentration of 5 μM;
 TGFβ inhibitor SB431542: at a final concentration of 2 μM;
 Retinoic acid (RA): at a final concentration of 5 μM.

(13) Composition 13 for Tumor Cell Transdifferentiation Accompanied by Apoptosis
 GSK3β inhibitor CHIR-99021: at a final concentration of 4 μM;
 TGFβ inhibitor A83-01 at a final concentration of 3 μM;
 Retinoic acid (RA): at a final concentration of 0.5 μM;
 BrdU: at a final concentration of 15 μM.

(14) Composition 14 for Tumor Cell Transdifferentiation Accompanied by Apoptosis
 GSK3β inhibitor CHIR-99021: at a final concentration of 3 μM;
 TGFβ inhibitor SB431542: at a final concentration of 5 μM;

Retinoic acid (RA): at a final concentration of 3 μM;
BMP inhibitor LDN-193189: 0.5 μM;
EdU: at a final concentration of 30 μM.

(15) Composition 15 for Tumor Cell Transdifferentiation Accompanied by Apoptosis
GSK3β inhibitor BIO: at a final concentration of 3 μM;
TGFβ inhibitor SB431542: at a final concentration of 7.5 μM;
BMP inhibitor LDN-193189: at a final concentration of 0.5 μM.

(16) Composition 16 for Tumor Cell Transdifferentiation with Accompanying Apoptosis
GSK3β inhibitor CHIR-99021: at a final concentration of 5 μM;
TGFβ inhibitor LY2109761: at a final concentration of 2 μM;
Retinoic acid (RA): at a final concentration of 5 μM.

(17) Composition 17 for Tumor Cell Transdifferentiation Accompanied by Apoptosis
GSK3β inhibitor CHIR-99021: at a final concentration of 3 μM;
TGFβ inhibitor RepSox: at a final concentration of 7.5 μM;
BMP inhibitor LDN-193189: at a final concentration of 0.5 μM.

(18) Composition 18 for Tumor Cell Transdifferentiation Accompanied by Apoptosis
GSK3β inhibitor CHIR-98014: at a final concentration of 3 μM;
TGFβ inhibitor A83-01: at a final concentration of 5 μM;
BMP inhibitor LDN-193189: 2 μM.

(19) Composition 19 for Tumor Cell Transdifferentiation Accompanied by Apoptosis
GSK3β inhibitor CHIR-99021: at a final concentration of 4 μM;
TGFβ inhibitor SB431542: at a final concentration of 3 μM;
9-cis retinoic acid: at a final concentration of 0.5 μM.

(20) Composition 20 for Tumor Cell Transdifferentiation Accompanied by Apoptosis
GSK3β inhibitor TWS119: at a final concentration of 4 μM;
TGFβ inhibitor A83-01: at a final concentration of 3 μM;
Retinoic acid (RA): at a final concentration of 0.5 μM.

The small molecule compositions were each dissolved in DMSO to obtain concentrated solutions according to the process of step (1) described above in the "Culture method" portion.

2. Preparation of the Culture Media for Tumor Cell Transdifferentiation Accompanied by Apoptosis The DMSO concentrated solutions of Compositions 1-20 for tumor cell transdifferentiation accompanied by apoptosis as formulated above in step 1 were prepared according to the process of step (2) described above in the "Culture method" portion (using basal culture medium DMEM/F12) to obtain Media 1-20 for tumor cell transdifferentiation accompanied by apoptosis (that is, the final concentrations of the components in Composition 1 were the same as those in Medium 1; the final concentrations of the components in Composition 2 were the same as those in Medium 2; . . . the final concentrations of the components in Composition 20 were the same as those in Medium 20).

3. Preparation of Injection or Oral Formulations for Tumor Cell Transdifferentiation Accompanied by Apoptosis The components of the "Composition 8 for tumor cell transdifferentiation accompanied by apoptosis" as prepared above in step 1 were dissolved in 1% Captisol to obtain Agent 8 for injection or oral administration to experimental animals.

A "Composition 21 for tumor cell transdifferentiation accompanied by apoptosis" was formulated as follows, based on mg/kg (body weight):
GSK3 inhibitor CHIR-99021: 1 mg/kg;
TGFβ inhibitor SB431542: 0.5 mg/kg;
Retinoic acid (RA): 0.2 mg/kg;
BMP inhibitor LDN-193189: 0.2 mg/kg;

The specified components were dissolved in 1% Captisol to obtain an Agent 21 for injection or oral administration to experimental animals.

Example 2. Induced Transdifferentiation Accompanied by Apoptosis in Hepatoma Cells SMMC-7721 Using Medium 6

1. Culturing of Tumor Cells Inducing Transdifferentiation Accompanied by Apoptosis Hepatoma cells SMMC-7721 were suspended in the above-prepared Medium 6 and plated to prepare the treatment group.

The same volume (as in the treatment group) of DMSO (dimethyl sulfoxide) was added to the basal cell culture medium DMEM/F12 supplemented with 10% calf serum and 1% penicillin-streptomycin mix (100×) to obtain a DMSO "control medium" (percentages all refer to "% (v/v)"). Then, the same number (as treatment group) of hepatoma cells SMMC-7721 were suspended in the DMSO "control medium" and plated to prepare the control group.

The cells were cultured at 37° C. The culture medium was changed every 2-4 days. The cells were subcultured every 3-7 days.

2. Continuous Passage Culture of Hepatoma Cells for Transdifferentiation Accompanied by Apoptosis Process of the continuous passage culture: the original culture medium was discarded, and the cells were rinsed once with PBS. A digestion solution was added and the cells were digested at 37° C. for 1-5 minutes. After the digestion, the cells were centrifuged and the supernatant was discarded. The cell pellets were resuspended and plated at a ratio of 1:1-1:3 for continuous passage culture. The cells were cultured according to items 1 and 2 of Experiment Procedure wherein the culture medium was changed every 2-4 days. The digestion solution comprised trypsin (EDTA, Acutase, TrypleE, etc. can also be used). Cells were subcultured every 3-7 days.

3. Hepatocyte-Like Cells were Obtained Via Culture for Transdifferentiation Accompanied by Apoptosis After the culture for transdifferentiation accompanied by apoptosis and the passage culture for 1-3 weeks according to steps 1 and 2, apoptotic cells were removed by centrifugation. The non-apoptotic hepatoma cells were found transdifferentiated into non-oncogenic hepatocyte-like cells. The obtained non-oncogenic hepatocyte-like cells can be used in further scientific experiments.

Figure 1:
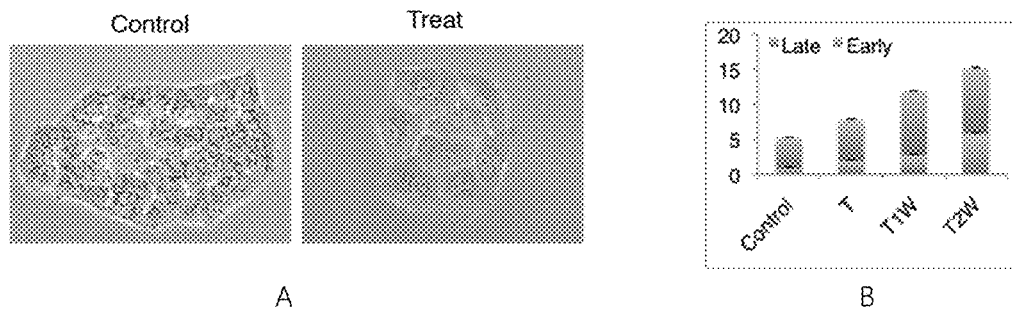
FIG. 1. Induced transdifferentiation of hepatoma cells SMMC-7721 into non-oncogenic cells and accompanying apoptosis by using small molecules (Medium 6).

Results are as shown in FIG. 1. A: hepatoma cells SMMC-7721 were transdifferentiated by induction, as evidenced by the substantial change in morphology; B: statistics of the induced transdifferentiation accompanied by apoptosis in hepatoma cells SMMC-7721. Different degrees of early and late apoptosis were observed in the treatment group at different stages of the treatment. In the control group, almost no apoptosis was observed, and partial natural late apoptosis was observed.

Example 3. Transdifferentiation Accompanied by Apoptosis in Hepatoma Cells HepG2 Induced Using Small Molecule Combinations (Media 1, 4)

The treatment and the control groups, as well as the experimental processes, were set according to Example 2, except that the Medium 6 was replaced by the Medium 1 or the Medium 4.

Results after culturing for 1-3 weeks are as shown in FIG. 2. A: hepatoma cells HepG2 (cultured in Medium 4) were transdifferentiated by induction, as evidenced by the substantial change in morphology. Except for the hepatoma cells subject to early or late apoptosis, the other hepatoma cells were all transdifferentiated. B: statistics of induced apoptosis in hepatoma cells HepG2 (in Medium 1). Different degrees of early and late apoptosis were observed in the treatment group at different stages of the treatment. In the control group, almost no apoptosis was observed, and partial natural late apoptosis was observed.

Example 4. 5-Fu-Resistant Hepatoma Cells 7402/5-Fu were Induced to Transdifferentiation Accompanied by Apoptosis Using Medium 5 or Medium 2

The treatment and the control groups, as well as the experimental processes, were as described in Example 2, except that Medium 6 was replaced by Medium 5 or Medium 2.

Results after culturing for 1-4 weeks are as shown in FIG. 3. A: hepatoma cells 7402/5-Fu (right) were transdifferentiated into hepatocyte-like cells under induction using Medium 5, as evidenced by the substantial change in morphology. B: statistics of induced transdifferentiation and apoptosis in hepatoma cells 7402/5-Fu using Medium 2. Different degrees of early and late apoptosis were observed in the treatment group at different stages of the treatment. In the control group, almost no apoptosis was observed, and partial natural late apoptosis was observed.

Example 5. Induced Transdifferentiation of Hepatoma Cells SMMC-7721, HepG2, 7402/5-Fu into Hepatocyte-Like Cells that are Functional as Normal Hepatocytes Using Medium 6, 4 or 5

The treatment and the control groups, as well as the experimental processes, were as described in Examples 2, 3 and 4, except that Media 6, 4 and 5 were used instead. The treatment groups were cultured for 2 weeks before centrifugation to remove apoptotic cells. The non-apoptotic hepatoma cells were found transdifferentiated into non-oncogenic hepatocyte-like cells. The cells in the control groups were harvested at the same time point.

(1) Liver Glycogen Staining

The Schiff method was used. Specifically, (1) the culture medium was discarded and the cells were rinsed once with PBS; (2) 4% paraformaldehyde was added to fix for 10 min, and then the cells were rinsed with PBS for 5 min×3 times; (3) PAS-I liquid was added to react for 10 min, followed by washing with running water; (4) PAS-II liquid was added to react for 1-2 min, followed by washing with running water; (5) microscopic observation and photography were conducted.

(2) Oil-Red Staining

Detection was carried out using the kit purchased from Nanjing Jiancheng Technology Co., Ltd, Cat. No. D027. Detailed procedures were as specified in the manufacturer's instruction.

The results are as shown in FIG. 4. Hepatoma cells SMMC-7721 (Medium 6), HepG2 (Medium 4), 7402/5-Fu (Medium 5) were transdifferentiated under induction. The obtained hepatocyte-like cells are functional as normal hepatocytes. PAS: glycogen staining; Oil-red: oil-red staining, reflecting fat uptake.

Accordingly, the hepatocyte-like cells obtained via transdifferentiation of hepatoma cells exhibited corresponding functions of normal human hepatocytes.

Example 6. Induced Transdifferentiation of Hepatoma Cells SMMC-7721, HepG2, 7402/5-Fu into Hepatocyte-Like Cells that are Functional as Normal Hepatocytes Using Medium 10, 11 or 12

The treatment and the control groups, as well as the experimental processes, were set according to Example 2, except that Media 10, 11 and 12 were used instead. The treatment groups were cultured for 2 weeks before centrifugation to remove apoptotic cells. The non-apoptotic hepatoma cells were found transdifferentiated into non-oncogenic hepatocyte-like cells. Cells in the control groups were harvested at the same time point.

(1) Albumin Secretion (ALB) Assay and Urea Production (Urea) Assay

Cells in the treatment and the control groups were assayed for albumin secretion (ALB) and urea production (Urea) by ELISA using the BCG Albumin assay kit (Bioassay System/DIAG-250) and the Urea assay kit (Bioassay System/DIUR-500). Detailed procedures are as specified in the manufacturer's instruction.

(2) P450 Enzyme (CYP3A4 and CYP1A2) Activity Induction Assay

Rifampicin (for induction of CYP3A4) and Omeprazole (for induction of CYP1A2) were respectively used to induce the corresponding P450 enzymatic activities. Different concentrations of Rifampicin (1 μM, 10 μM, 25 μM) and Omeprazole (1 μM, 10 μM, 25 μM) were added into cell cultures of the treatment and the control groups for 48 hrs. Cellular RNA was harvested and assayed for CYP3A4 and CYP1A2 gene expression under different treatment conditions using qRT-PCR.

Results are as shown in FIG. 5.

A: hepatoma cells SMMC-7721 were transdifferentiated under induction (Medium 10) into hepatocyte-like cells that were functional as normal hepatocytes;

B, hepatoma cells HepG2 were transdifferentiated under induction (Medium 11) into hepatocyte-like cells that are functional as normal hepatocytes;

C, 5-Fu-resistant hepatoma cells 7402/5-Fu were transdifferentiated under induction (Medium 12) into hepatocyte-like cells that are functional as normal hepatocytes;

The Blue columns correspond to early apoptosis and the red columns to late apoptosis. T1W, T2W, T3W refer to 1-week, 2-week and 3-week treatments, respectively. Rif: Rifampicin; Ome: Omeprazole.

As seen, the obtained hepatocyte-like cells exhibited corresponding functions of normal human hepatocytes. The transdifferentiated hepatoma cells retrieved functions of normal hepatocytes in terms of albumin secretion (ALB), urea production (Urea), CYP1A2 induction and CYP3A4 induction.

Example 7. Hepatoma Cells SMMC-7721, HepG2 and 7402/5-Fu were Transdifferentiated by Induction (Using Medium 6, 4 or 5) into Hepatocyte-Like Cells that Lost Oncogenicity In Vivo and In Vitro The treatment and the control groups, as well as the experimental processes, were set according to Example 2, except that Media 6, 4 and 5 were used instead. The treatment groups were cultured for 2 weeks before centrifugation to remove apoptotic cells. The non-apoptotic hepatoma cells were found transdifferentiated into hepatocyte-like cells that lost oncogenicity in vivo and in vitro.

1. In vitro Assay of Oncogenicity in the Hepatocyte-like Cells Obtained from Transdifferentiation Process: Cells of the treatment and the control groups were inoculated onto a 6-well plate at the amount of $1\times10^3$ cells, and then cultured for 2 weeks according to Example 2. The cells were stained using crystal violet, photographed, observed and counted for colony formation. The results are as shown in FIG. 6. A: the hepatocyte-like cells obtained by the induced transdifferentiation of hepatoma cells SMMC-7721 (Medium 6), HepG2 (Medium 4) and 7402/5-Fu (Medium 5) exhibited zero colony formation, which suggests loss of oncogenicity in vitro.

2. Subcutaneous Tumor-Bearing Experiment with Hepatocyte-like Cells Obtained from Transdifferentiation Hepatocyte-like cells obtained from a 20-day transdifferentiation of hepatoma cells were digested with digestion solution into single cells, which were then centrifuged, rinsed with PBS, and counted. $1\times10^6$ cells were injected subcutaneously into the right hind leg of a 5-week-old nude mouse, and the cancer cells treated with DMSO "control medium" for the same duration were injected subcutaneously as control into the left hind leg of same nude mouse. 4 weeks later, at the end of the experiment, tumors were excised and photographed. Results are as shown in FIG. 6. B: the non-oncogenic hepatocyte-like cells obtained by the induced transdifferentiation of hepatoma cells SMMC-7721 using Medium 6 exhibited no tumor formation in vivo, which suggests loss of oncogenicity in vivo. C: the non-oncogenic hepatocyte-like cells obtained by the induced transdifferentiation of hepatocellular carcinoma 7402/5-Fu using Medium 8 exhibited no tumor formation in vivo, which suggests loss of oncogenicity in vivo. Top: cells from the treatment group did not form tumor in the hind leg (right), which suggests loss of oncogenicity; cells from the control group (left) induced tumor formation. Bottom image exhibits the anatomic appearance of the tumors formed in the control.

Example 8. Assay of Patient's Hepatoma Tissue in PDX Animal Model (Composition 8 for Transdifferentiation Accompanied by Apoptosis)

Tumor tissue resectted from a patient having hepatoma was implanted subcutaneously into 5-week-old nude mice for tumor formation (PDX model). The tumors formed subcutaneously were excised and re-implanted subcutaneously into 5-week-old nude mice for tumor formation. The drug treatment started when the tumors reached 5-10 mm in size. Agent 8 as formulated in Example 1 was administrated by intratumor injection, 3 times a week. DMSO saline injection was used as control. The experiment was terminated 4 weeks later. The tumors were isolated and photographed, and the tumor tissues were fixed and HE stained. Results are as shown in FIG. 7. Tumor tissue and cell necrosis, disruption or loss of structural integrity were observed in the treatment group, while no change in tumor tissues and cellular structure in the control group.

Example 9. The Effects of Medium 8 and Medium 3 on Normal Human Fibroblasts and Hepatocytes The treatment and the control groups, as well as the experimental processes, were set according to Example 2, except that normal human fibroblasts and hepatocytes were treated with Medium 8 or 3.

Results are as shown in FIG. 8. After cultured for 3 weeks, the normal human fibroblasts and hepatocytes exhibited no change in morphology, compared with the control group, which suggests that they were not affected by the treatment.

Example 10. Induced Transdifferentiation Accompanied by Apoptosis in Nasopharyngeal Carcinoma Cells HNE and Lung Carcinoma Cells H460 Using Medium 9 or 7

The treatment and the control groups, as well as the experimental processes, were set according to Example 2. The results obtained after a 2-week treatment, the results are as shown in FIG. 9.

Nasopharyngeal carcinoma cells HNE in the treatment group (treated with Medium 9) were transdifferentiated under induction, as evidenced by the substantial change in morphology. Lung carcinoma cells H460 in the treatment groups were treated with Medium 9 or 7, wherein the lung carcinoma cells H460 treated with Medium 7 exhibited a nearly complete apoptosis by induction, while almost no apoptosis was observed in lung carcinoma cells H460 in the control group.

Example 11. Induced Transdifferentiation Accompanied by Apoptosis in Gastric Cancer Cells SGC-7901 and MKN28 Using Medium 12 or 13

The treatment and the control groups, as well as the experimental processes, were set according to Example 2.

The results obtained after a 2-week treatment are as shown in FIG. 10. Gastric cancer cells SGC-7901 (Medium 12) and MKN28 (Medium 13) were transdifferentiated under induction, as evidenced by the substantial change in morphology.

Example 12. Induced Transdifferentiation in Pancreatic Cancer Cells SW1990 Using Medium 12

The treatment and the control groups, as well as the experimental processes, were set according to Example 2.

The results obtained in pancreatic cancer cells SW1990 with the treatment using Medium 12 for 2 weeks are as shown in FIG. 11. The cancer cells in the treatment group were transdifferentiated, as evidenced by the substantial change in morphology.

Example 13. Induced Transdifferentiation in Breast Carcinoma Cells SKBr3 Using Medium 13

The treatment and the control groups, as well as the experimental processes, were set according to Example 2. The results obtained with the treatment using Medium 13 for 2 weeks are as shown in FIG. 12. The breast carcinoma cells SKBr3 in the treatment group were transdifferentiated, as evidenced by the substantial change in morphology.

Example 14. Induced Transdifferentiation in Leukemia Cells U937, B Cell Lymphoma SUDHL-4 Using Medium 10 or 11

The treatment and the control groups, as well as the experimental processes, were set according to Example 2. The results obtained with the treatment for 2 weeks are as shown in FIG. 13. The leukemia cells U937 (Medium 10) and the B cell lymphoma SUDHL-4 (Medium 11) exhibited massive apoptosis.

Example 15. Induced Transdifferentiation in Breast Carcinoma Cells SKBr3 and Gastric Cancer Cells MKN28 Using Medium 13 or 14

The treatment and the control groups, as well as the experimental processes, were set according to Example 2. The results obtained with the treatment for 2 weeks are as shown in FIG. 14. The breast carcinoma cells SKBr3 (Medium 13) and the gastric cancer cells MKN28 (Medium 14) were transdifferentiated under induction, as evidenced by the substantial change in morphology.

Example 16. Induced Transdifferentiation of Intestinal Carcinoma Cells HCT116 into Non-Oncogenic Cells Using Medium 9

The treatment and the control groups, as well as the experimental processes, were set according to Example 2. The results obtained with the treatment for 2 weeks are as shown in FIG. 15. Right: in the intestinal carcinoma cells HCT116 in the treatment group (treated with Medium 9), colony formation is halted, which suggests loss of oncogenicity.

Example 17. Prostatic Carcinoma Cells PC-3, Ovarian Carcinoma Cells SKOV3 and A2780 Lost Oncogenicity after the Transdifferentiation Induced Using Medium 5, 7 or 8

The treatment and the control groups, as well as the experimental processes, were set according to Example 7. Results obtained with the treatment for 2 weeks are as shown in FIGS. 16 and 17. The image on the right in FIG. 16 and images on the right in FIG. 17 show that prostatic carcinoma cells PC-3 (Medium 5), ovarian carcinoma cells SKOV3 (Medium 7) and A2780 (Medium 8) did not form colony after the induced transdifferentiation and lost oncogenicity.

Example 18. Gastric Cancer Cells MKN28, Breast Carcinoma Cells SKbr3 Lost Oncogenicity after the Transdifferentiation Induced Using Medium 10 or 11

The treatment and the control groups, as well as the experimental processes, were set according to Example 7. Results obtained with the treatment for 2 weeks are as shown in FIG. 18. The images on the right side in FIG. 18 show that gastric cancer cells MKN28 (Medium 10) and breast carcinoma cells SKbr3 (Medium 11) did not form colony after the induced transdifferentiation and lost oncogenicity.

Example 19. Induced Transdifferentiation Accompanied by Apoptosis in Glioma Cells T98G, U87MG Using Medium 4 or 5

The treatment and the control groups, as well as the experimental processes, were set according to Example 14. Results obtained with the treatment for 2 weeks are as shown in FIG. 19. The images on the right side in FIG. 18 show that glioma cells T98G (Medium 4) and U87MG (Medium 5) were transdifferentiated under induction, as evidenced by the substantial change in morphology.

Example 20. Assay of Patient's Hepatic Carcinoma Tissue in PDX Animal Model (Small Molecule Composition 15 for Tumor Cell Transdifferentiation Accompanied by Apoptosis)

The injection to experimental animals, the treatment and the control groups, as well as the experimental and staining processes, were set according to Example 8, except that Agent 15 for injection formulated from Composition 15 for tumor cell transdifferentiation accompanied by apoptosis was used instead. Results are as shown in FIG. 20.

After being treated using Agent 15 for 3 weeks, the hepatic carcinoma tissue and cells in the treatment group exhibited massive necrosis and disruption or loss in cancerous structure integrity (left image). After being treated with the small molecule agent for 3 weeks, the remaining tissues and cells exhibited expression of human hepatocyte-specific marker HNF4a, which suggests that the cells were transdifferentiated (right image).

Example 21. Lung Carcinoma Cells A549, H1299 and H460 Lost Oncogenicity In Vivo and In Vitro after Transdifferentiation Induced Using Medium 14, 13 or 9

The injection to experimental animals, the treatment and the control groups, as well as the experimental and staining processes, were set according to Example 7. Results are as shown in FIG. 21.

A: results obtained with the treatment for 2 weeks, wherein the bottom images show that lung carcinoma cells A549 (Medium 14), H1299 (Medium 13) and H460 (Medium 9) in the treatment groups did not form colony after the induced transdifferentiation and lost oncogenicity; B: the transdifferentiated lung carcinoma cells A549 (Medium 14) in the treatment group were injected into the right hind legs of nude mice (marked with blue arrows), and no tumor formation was observed in 4 weeks, which suggests loss of oncogenicity in vivo.

Example 22. Induced Transdifferentiation of Lung Carcinoma Cells H1299 into Non-Oncogenic Cells Using Medium 15

The treatment and the control groups, as well as the experimental processes, were set according to Example 2. The results obtained with the treatment for 2 weeks are as shown in FIG. 22. Right: lung carcinoma cells H1299 in the treatment group (treated with Medium 15) did not form colony after the induced transdifferentiation and lost oncogenicity.

It suggests that a different small molecule GSK3β inhibitor, BIO, in combination with a TGFβ inhibitor and a BMP inhibitor, can also induce the transdifferentiation accompanied by apoptosis in tumor cells.

Example 23. Induced Transdifferentiation of Ovarian Carcinoma Cells A2780, SKOV3 into Non-Oncogenic Cells Using Medium 16 or 17

The treatment and the control groups, as well as the experimental processes, were set according to Example 2.

The results obtained with the treatment for 2 weeks are as shown in FIG. 23. The images on the right side show that ovarian carcinoma cells A2780 (Medium 16), SKOV3 (Medium 17) did not form colony after the induced transdifferentiation and lost oncogenicity.

It suggests that different small molecule TGFβ inhibitors, LY2109761 and RepSox, in combination with a GSK3β inhibitor and a retinoid compound or a BMP inhibitor, can also induce the transdifferentiation accompanied by apoptosis in tumor cells.

Example 24. Induced Transdifferentiation in Prostatic Carcinoma Cells PC9 Using Medium 18

The treatment and the control groups, as well as the experimental processes, were set according to Example 2.

The results obtained with the treatment using Medium 18 for 2 weeks are as shown in FIG. 24. Right: prostatic carcinoma cells PC9 in the treatment group were transdifferentiated under induction, as evidenced by the substantial change in morphology.

It suggests that a different small molecule GSK3β inhibitor, CHIR-98014, in combination with TGFβ inhibitor and BMP inhibitor, can also induce the transdifferentiation accompanied by apoptosis in the tumor cells.

Example 25. Induced Transdifferentiation Accompanied by Apoptosis in Gastric Carcinoma SGC-7901 Cells Using Medium 19 or 20

1. Gastric carcinoma SGC-7901 cells lost oncogenicity after the transdifferentiation induced using Medium 19.

The treatment and the control groups, as well as the experimental processes, were set according to Example 2. The results obtained with the treatment for 2 weeks are as shown in FIG. 25. A: gastric carcinoma SGC-7901 cells in the treatment group did not form colony after the induced transdifferentiation and lost oncogenicity in vitro.

It suggests that a different small molecule retinoid compound, 9-cis retinoic acid, in combination with GSK3β inhibitor, TGFβ inhibitor, can also induce the transdifferentiation accompanied by apoptosis in the tumor cells.

2. Induced transdifferentiation accompanied by apoptosis in gastric carcinoma SGC-7901 cells using Medium 19 or 20

The treatment and the control groups, as well as the experimental processes, were set according to Example 2.

The statistics of the induced transdifferentiation accompanied by apoptosis obtained in gastric carcinoma SGC-7901 cells with the treatment for 2 weeks are as shown in FIG. 25. B: cells in the treatment group exhibited early and late apoptosis of different degrees at different time points of treatment. A small part of cells in the control group showed early and late natural apoptosis. The control and the treatment groups had statistically significant difference in resultant apoptosis ($p<0.005$).

It suggests that a different small molecule GSK3β inhibitor, TWS119, in combination with a TGFβ inhibitor and a retinoid compound, can also induce the transdifferentiation accompanied by apoptosis in the tumor cells.

Example 26. Pancreatic Carcinoma SW1990 Cells Lost Onocogenicity after the Transdifferentiation Induced Using Medium 16

The treatment and the control groups, as well as the experimental processes, were set according to Example 2. Results obtained with the treatment for 2 weeks are as shown in FIG. 26. Right: pancreatic carcinoma SW1990 cells in the treatment group (treated with Medium 16) did not form colony after the induced transdifferentiation, and lost oncogenicity in vitro.

It suggests that a different small molecule TGFβ inhibitor, LY2109761, in combination with a GSK3β inhibitor and a retinoid compound, can also induce the transdifferentiation accompanied by apoptosis in tumor cells.

All references mentioned in this application are incorporated by reference in this application, as if each article were individually incorporated by reference. In addition, it should be understood that after reading the above teachings of the present invention, those skilled in the art can make various changes or modifications to the present invention, and these equivalent forms also fall within the scope defined by the appended claims of the present application.

The invention claimed is:

1. A small molecule composition for chemically inducing reprogramming or transdifferentiation of human tumor cells directly into non-oncogenic cells and accompanying tumor cell apoptosis, wherein the composition comprises a GSK3β inhibitor and a TGFβ inhibitor; and wherein the composition excludes exogenous genes and transcription factors.

2. The composition of claim 1, wherein the
   GSK3β inhibitor is present at an amount of 0.046-4.65 parts by weight or at a final concentration of 0.1-10 μM in a solution; and wherein
   the TGFβ inhibitor is present at an amount of 0.038-7.68 parts by weight or at a final concentration of 0.1-20 μM in a solution.

3. The composition of claim 1, wherein the
   GSK3β inhibitor is present at an a amount of 0.232-2.325 parts by weight or at a final concentration of 0.5-5 μM in a solution; and wherein
   the TGFβ inhibitor is present at an amount of 0.192-3.84 parts by weight or at a final concentration of 0.5-10 μM in a solution.

4. The composition of claim 1, wherein the composition further comprises:
   a retinoid compound present at an amount of 0.03-6.0 parts, preferably 0.15-3 parts by weight or at a final concentration of 0.1-20 μM, preferably 0.5-10 μM in a solution.

5. The composition of claim 1, wherein the composition further comprises one or more components selected from the group consisting of:
   a BMP inhibitor present at an amount of 0.02-4.65 parts, preferably 0.203-2.03 parts by weight or at a final concentration of 0.05-10 μM, preferably 0.5-5 μM in a solution;
   BrdU present at an amount of 0.15-30 parts, preferably 1.5-15 parts by weight or at a final concentration of 0.5-100 μM, preferably 5-50 μM in a solution; and
   EdU present at an amount of 0.125-25 parts, preferably 1.25-12.5 parts by weight or at a final concentration of 0.5-100 μM, preferably 5-50 μM in a solution.

6. The composition of claim 1, wherein,
   the GSK3β inhibitor includes a GSK3β signaling pathway inhibitor or a compound of the same class that have the same function or target the same induction site(s), as represented by CHIR-99021, BIO, IM-12, TWS119, 1-Azakenpaullone, CHIR-98014, Tideglusib, AR-A014418, LY2090314, SB216763, AZD1080, or a functionally equivalent pharmaceutical preparation, analogue, isomer and/or salt, hydrate or precursor thereof, or a combination thereof; preferably, GSK3β inhibitor CHIR-99021; and
   the TGFβ inhibitor includes a TGFβ signaling pathway inhibitor or a compound of the same class that have the same function or target the same induction site(s), as represented by SB431542, A83-01, SB525334, LY2109761, RepSox, SD-208, GW788388, SB505124, EW-7197, or a functionally equivalent pharmaceutical preparation, analogue, isomer and/or salt, hydrate or precursor thereof, or a combination thereof; preferably, TGFβ inhibitor SB431542 or/and A83-01.

7. The composition of claim 1, wherein the composition is a pharmaceutical composition, further comprising a pharmacologically acceptable carrier or excipient, wherein the carrier or excipient includes:
- water, saline, phosphate buffer or any of other aqueous solvents;
- DMSO, glycerin and ethanol or any of other organic solvents;
- microspheres, liposomes, microemulsion or a polymeric surfactant;
- a colloidal drug delivery system or a polymer drug delivery system; or
- a preservative, antioxidant, flavoring agent, fragrance, solubilizer, emulsifier, pH buffer, adhesive, filler, lubricant, or any of other pharmaceutical excipients.

8. The composition of claim 1, wherein the composition allows preparation into dosage forms including:
- solid dosage forms, including powders, pulvis, tablets, pills, capsules, sustained release formulations, controlled-release formulations, and other solid dosage forms;
- liquid dosage forms, including injections, infusions, suspensions, and other liquid dosage forms;
- gaseous dosage forms; and
- semi-solid dosage forms.

9. The composition of claim 4, wherein the retinoid compound is a naturally occurring one or an artificially synthesized one, and includes a retinoid differentiation-inducing agent or a compound of the same class that have the same function or target the same induction site(s), as represented by retinoic acid, 13-cis retinoic acid, 9-cis retinoic acid, isotretinoin, etc., or a functionally equivalent pharmaceutical preparation, analogue, isomer and/or salt, hydrate or precursor thereof, or a combination thereof; preferably, retinoic acid.

10. The composition of claim 5, wherein the BMP inhibitor includes a BMP signaling pathway inhibitor or a compound of the same class that have the same function or targeting the same inductive site, as represented by LDN-193189, K02288, DMH1, etc., or a functionally equivalent pharmaceutical preparation, analogue, isomer and/or salt, hydrate or precursor thereof, or a combination thereof; preferably, BMP inhibitor LDN-193189.

11. A kit for inducing reprogramming or transdifferentiation of human tumor cells directly into non-oncogenic cells and accompanying tumor cell apoptosis, wherein the kit comprises the composition according to claim 1 or an anti-tumor drug or a medical formulation developed and manufactured based on the composition according to claim 1 or an agent or a culture medium prepared based on the composition according to claim 1.

12. A method for inducing reprogramming or transdifferentiation of tumor cells directly into non-oncogenic cells and accompanying tumor cell apoptosis, wherein the method includes treating the human tumor cells with the composition according to claim 1, so that the human tumor cells are reprogrammed directly into non-oncogenic cells, which is accompanied by tumor cell apoptosis.

13. The method of claim 12, wherein the tumors or tumor cells include but are not limited to: liver cancer, lung cancer, stomach cancer, colorectal cancer, pancreatic cancer, breast cancer, ovarian cancer, prostate cancer, osteosarcoma, lymphoma, leukemia, nasopharyngeal cancer, esophageal cancer, cervical cancer, oral cavity cancer, salivary gland tumor, nasal cavity and paranasal cavity sinus malignant tumor, laryngeal cancer, otic tumor, ocular tumor, thyroid tumor, mediastinal tumor, thoracic wall and pleural tumor, intestinal tumor, biliary tract tumor, pancreatic and periampullary tumor, mesenteric and retroperitoneal tumor, renal tumor, adrenal tumor, bladder tumor, testicular tumor, penile cancer, endometrial cancer, ovarian malignant tumor, malignant trophoblastic tumor, vulvar and vaginal cancer, malignant lymphoma, multiple myeloma, soft tissue tumor, bone tumor, skin and adnexal tumor, malignant melanoma or nervous system tumors and other hematological and solid tumors or cells thereof; preferably liver cancer or hepatoma cells.

* * * * *